(12) United States Patent
Amara et al.

(10) Patent No.: US 7,427,469 B2
(45) Date of Patent: Sep. 23, 2008

(54) METHOD OF TREATING CYTOMEGALOVIRUS WITH DC-SIGN BLOCKERS

(75) Inventors: Ali Amara, Paris (FR); Frank Halary, Bordeaux (FR); Julie Dechanet-Merville, Merignac (FR); Jean-Francois Moreau, Merignac (FR); Fernando Arenzana-Seisdedos, Nevron (FR); Thierry Delaunay, Le Haillan (FR)

(73) Assignee: Institut Pasteur, Paris (FR)

( * ) Notice: Subject to any disclaimer, the term of this patent is extended or adjusted under 35 U.S.C. 154(b) by 365 days.

(21) Appl. No.: 10/700,507

(22) Filed: Nov. 5, 2003

(65) Prior Publication Data

US 2004/0141968 A1    Jul. 22, 2004

Related U.S. Application Data

(60) Provisional application No. 60/425,324, filed on Nov. 12, 2002, provisional application No. 60/423,581, filed on Nov. 5, 2002.

(51) Int. Cl.
*C12Q 1/70* (2006.01)
*A61K 39/245* (2006.01)

(52) U.S. Cl. .................. 435/5; 435/7.1; 424/230.1

(58) Field of Classification Search .............. 435/5, 435/7.1, 7.2, 7.94, 325, 363, 366; 424/130.1, 424/141.1, 159.1, 208.1, 230.1, 141, 208
See application file for complete search history.

(56) References Cited

U.S. PATENT DOCUMENTS

| | | | |
|---|---|---|---|
| 4,522,811 A | 6/1985 | Eppstein et al. | |
| 4,683,195 A | 7/1987 | Mullis et al. | |
| 4,683,202 A | 7/1987 | Mullis | |
| 5,223,409 A | 6/1993 | Ladner et al. | |
| 5,403,484 A | 4/1995 | Ladner et al. | |
| 5,498,538 A | 3/1996 | Kay et al. | |
| 5,516,637 A | 5/1996 | Huang et al. | |
| 5,565,332 A | 10/1996 | Hoogenboom et al. | |
| 5,567,582 A * | 10/1996 | Grundy et al. | 435/5 |
| 5,571,698 A | 11/1996 | Ladner et al. | |
| 5,625,033 A | 4/1997 | Kay et al. | |
| 5,658,727 A | 8/1997 | Barbas et al. | |
| 5,667,988 A | 9/1997 | Barbas et al. | |
| 6,391,567 B1 | 5/2002 | Littman et al. | |
| 2004/0197330 A1 | 10/2004 | Amara et al. | |

FOREIGN PATENT DOCUMENTS

| | | | |
|---|---|---|---|
| NL | EP 1046651 A1 * | 10/2000 | |
| WO | WO 91/05876 A1 * | 5/1991 | |
| WO | WO 93/01820 | 2/1993 | |
| WO | WO 00/63251 | 10/2000 | |
| WO | WO 01/64752 A2 | 9/2001 | |
| WO | WO 02/080851 A2 | 10/2002 | |

OTHER PUBLICATIONS

Desrosiers, R. Prospects for an AIDS vaccine, Nature Medicine, 2004, 10(3):221-223.*
Feinberg et al. AIDS vaccine models: challenging challenge viruses, Nature Medicine, 2002, 8(3):207-210.*
Greene, W. The brightening future of HIV therapeutics, Nature Immunology, 2004, 5(9):867-871.*
Wang et al. Recombinant Modified Vaccinia Virus Ankara Expressing a Soluble Form of Glycoprotein B, 2004, 78(8):3965-3976.*
MacDonald et al. Mucosal and Parenteral Vaccination against Acute and Latent MCMV, J. Virology, 1998, 72(1):442-451.*
Centers for Disease Control, National Center for Infectious Diseases Cytomegalovirus Infection, website last updated 2002 http://www.cdc.gov/ncidod/diseases/cmv.htm.*
Pass et al., The Journal of Infectious Diseases, 1999, 180:970-975.*
Cunningham et al. The New England Journal of Medicine, 1998, 339(4):236-244.*
Geijtenbeek et al. Cell, 2000, 100:587-597.*
Kwon et al.; "DC-Sign-Mediated Internalization of HIV is Required for *Trans*-Enhancement of T Cell Infection"; *Immunity*, vol. 16, No. 1, pp. 135-144, (2002).
Navarro-Sanchez et al.; "Dendritic-Cell-Specific ICAM3-Grabbing Non-Integrin is Essential for the Productive Infection of Human Dendritic Cells by Mosquito-Cell-Derived Dengue Viruses"; EMBO Reports, vol. 4, No. 7, pp. 723-728, (2003).
Tassaneetrithep et al.; "DC-SING (CD209) Mediates Dengue Virus Infection of Human Dendritic Cells"; Journal of Experimental Medicine, vol. 197, No. 7, pp. 823-829, (2003).
Men et al. Identification of Chimpanzee fab Fragments, Journal of Virology, 2004, 78(9): 4665-4674.
Brandriss et al. "Lethal 17D Yellow Fever Encephalitis in Mice", Journal of General Virology, 1986, 67:229-234.
Lyssen et al., Perspectives for the Treatment of Infections with Flavivirdae, Clinical Microbiology Reviews, 2000, 13(1):67-82.

(Continued)

*Primary Examiner*—Stacy B Chen
(74) *Attorney, Agent, or Firm*—Finnegan, Henderson, Farabow, Garrett, and Dunner, L.L.P.

(57) ABSTRACT

The present invention relates to methods and compositions for preventing or treating diseases of a mammal, including viral infections, wherein at least one symptom of the disease is mediated at least in part by the binding of an effector molecule to a DC-SIGN receptor present on cells of the mammal to be treated. The invention also provides methods of identifying compositions, wherein the compositions are useful for treating mammalian diseases, including viral infections, for which at least one symptom of the disease is mediated at least in part by the specific binding of an effector molecule to a DC-SIGN receptor present on the cells that express the DC-SIGN receptor, belonging to the mammal to be treated. The invention further relates to compositions and methods for targeting subject molecules to cells that express the DC-SIGN receptor.

12 Claims, 7 Drawing Sheets

OTHER PUBLICATIONS

Figure 1:
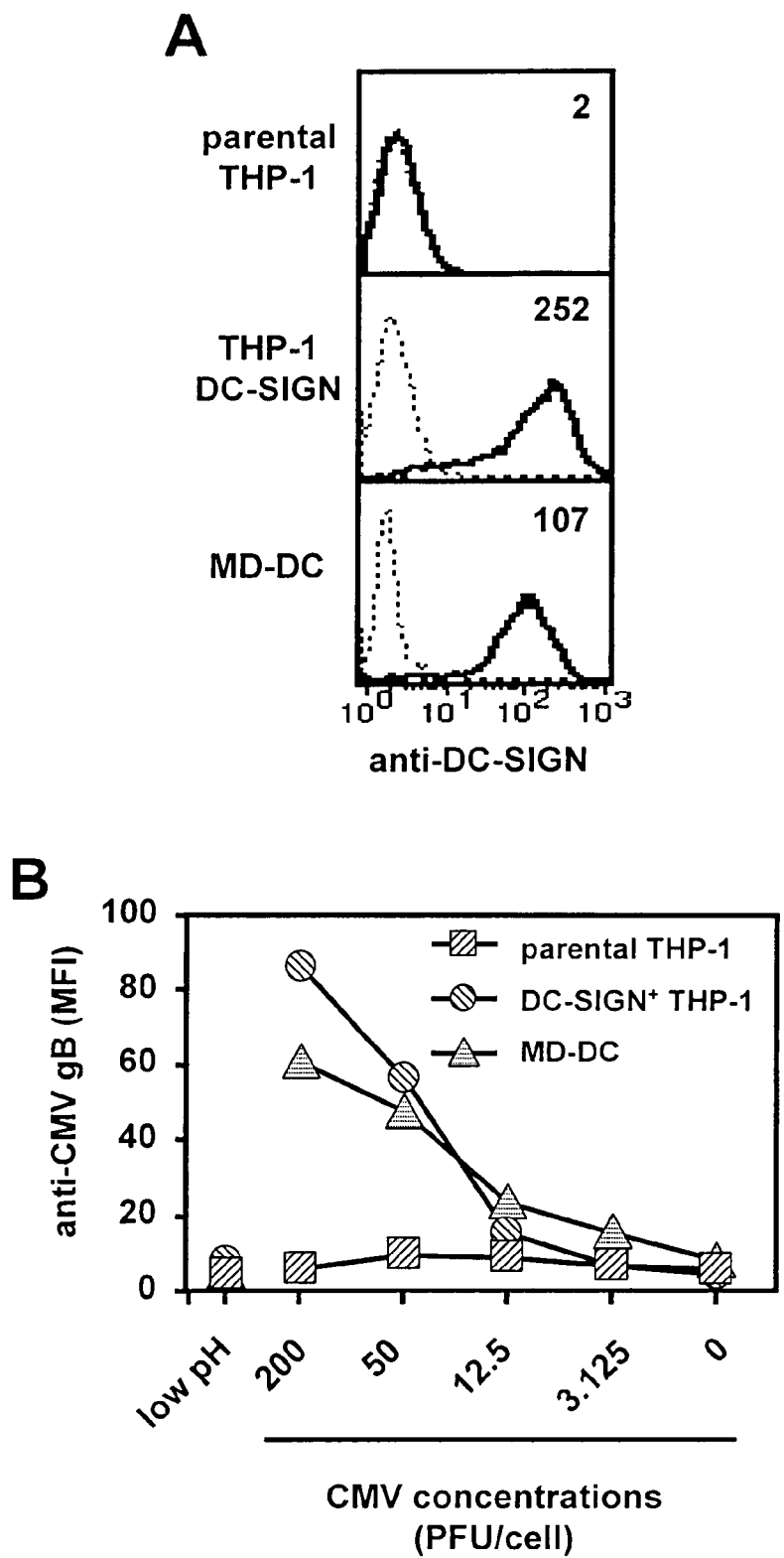

U.S. Appl. No. 10/464,531 of Oliver Neyrolles, Oliver Schwartz, Ludvic Tailleux, and Philippe Lagrange, filed Jun. 19, 2003.

U.S. Appl. No. 10/533,924 of Ali Amara et al., filed May 4, 2005, as a 371 of PCT/IB2003/005569, filed Nov. 5, 2003.

Office Action dated Dec. 28, 2004, in U.S. Appl. No. 10/700,491.

Office Action dated Jul. 26, 2005, in U.S. Appl. No. 10/700,491.

Office Action mailed Jun. 7, 2006, in U.S. Appl. No. 10/700,491, which was filed Nov. 5, 2003.

Curtis, Benson M. et al., "Sequence and Expression of a Membrane-Associated C-type Lectin that Exhibits CD4-Independent Binding of Human Immunodeficiency Virus Envelope Glycoprotein gp120," *Proc. Natl. Acad. Sci. USA*, vol. 89, pp. 8356-8360 (1992).

Geijtenbeek, Teunis B.H. et al., "Identification of DC-Sign, a Novel Dendritic Cell-Specific ICAM-3 Receptor that Supports Primary Immune Responses," *Cell*, vol. 100, pp. 575-585 (2000).

Halary, Franck et al., "Human Cytomegalovirus Binding to DC-Sign is Required for Dendritic Cell Infection and Target Cell *trans*-Infection," *Immunuty*, vol. 17, pp. 653-664 (2002).

Tailleux, Ludovic et al., "DC-Sign is the Major Mycobacterium Tuberculosis Receptor on Human Dendritic Cells," *The Journal of Experimental Medicine*, vol. 197, pp. 121-127 (2003).

U.S. Appl. No. 10/464,531 of Olivier Neyrolles, Olivier Schwartz, Ludovic Tailleux, and Philippe Lagrange, filed Jun. 19, 2003.

U.S. Appl. No. 10/700,507 of Ali Amara, Frank Halary, Julie Dechanet-Merville, Jean-Francois Moreau, Fernando Arenzana-Seisdedos and Thierry Delaunay, filed Nov. 5, 2003.

* cited by examiner

METHOD OF TREATING CYTOMEGALOVIRUS WITH DC-SIGN BLOCKERS

Applicants claim the right to priority under 35 U.S.C. § 119(e) based on Provisional Patent Application Nos. 60/423,581, filed Nov. 5, 2002, and 60/425,324, filed Nov. 12, 2002, both of which are incorporated herein by reference in their entirety.

BACKGROUND OF THE INVENTION

1. Field of the Invention

This invention relates to methods and compositions for preventing or treating diseases of a mammal, wherein at least one symptom of the disease is mediated at least in part by the binding of an effector molecule to a DC-SIGN receptor of the mammal to be treated. The effector molecule may be a molecule on a foreign organism. The foreign organism may be a virus.

The invention also relates to compositions, and to methods of identifying compositions, wherein the compositions are useful for treating mammalian diseases for which at least one symptom of the disease is mediated at least in part by the binding of an effector molecule to a DC-SIGN receptor of the mammal to be treated.

The invention further relates to compositions and methods for targeting subject molecules to cells expressing DC-SIGN receptors, such as dendritic cells. These compositions and methods are based on targeting complexes, in which one or more subject molecules are covalently attached to one or more DC-SIGN blockers and, by virtue of binding of one or more of the DC-SIGN blockers of the targeting complex to DC-SIGN, the subject molecule is targeted to cells expressing DC-SIGN receptors.

2. Description of the Related Art

Human Cytomegalovirus (CMV) is a double strand DNA virus belonging to the Herpesviridae family and a ubiquitous pathogen in humans. CMV interaction with its host is characterized by a primary infection followed by lifelong persistence in the host organism and viral reactivation episodes. CMV infection is asymptomatic in most immunocompetent individuals because of an efficient anti-viral immune response. In contrast, CMV remains a major cause of morbidity and mortality in newborn and immunocompromised patients, namely in organ-transplanted recipients or AIDS patients. In many cases, CMV disease is characterized by a wide viral spread toward multiple organs (i.e. salivary glands, lung, kidney, gastrointestinal tract, liver, retina, CNS).

In vitro, a number of cell types are susceptible to CMV infection when considering virus entry and viral immediate early gene expression. However, full replication of virus DNA and subsequent production of infectious virions is limited to permissive cells (i.e. fibroblasts, endothelial cells, the U373 MG astrocytoma cell line, etc.; see for review Plachter et al., 1996). In fibroblasts (the prototypic cell type for in vitro studies of CMV infection) CMV entry occurs in sequential steps involving several viral envelope (Env) glycoproteins. Initial attachment of virus to host cells is mediated through interaction between Env glycoproteins gB (CMV gB) and/or CMV gM with cell surface heparan sulfate proteoglycans (Compton et al., 1993; Kari and Gehrz, 1992). Thereafter, binding of CMV gB with non-heparin cellular receptors probably allows more stable attachment of virus to cell surface (Boyle and Compton, 1998). Subsequent pH-independent fusion events between viral envelope and cell membrane are necessary for viral entry (Compton et al., 1992; Milne et al., 1998). Cell proteins involved in CMV attachment and/or fusion have not been identified precisely although two candidates have been proposed. The first one is annexin II which interacts with CMV gB (Pietropaolo and Compton, 1997). The second one is a 92.5 kDa protein binding to CMV gH (Baldwin et al., 2000). Fusion events are followed by penetration of the capsid which is transported to the nucleus. In some permissive cells, such as retinal pigment epithelial cells, CMV can also penetrate into cells by a mechanism of endocytosis (Bodaghi et al., 1999).

Recently, dendritic cells (DC), which are refractory to infection by laboratory-adapted CMV strains, were shown to be permissive to CMV infection and replication when infected with primary, clinical viral isolates (Riegler et al., 2000).

Dendritic cells are a diverse population of morphologically similar cell types found in lymphoid or non-lymphoid tissues. Dendritic cells function as antigen-presenting cells that efficiently capture antigens in the peripheral tissues and process them to form MHC-peptide complexes. After antigen uptake, these immature dendritic cells acquire the unique capacity to migrate from the periphery to the T cell areas of the secondary lymphoid organs. Dendritic cells convert antigens from foreign cells and infectious microorganisms into short peptides that are bound to membrane proteins of the major histocompatibility complex (MHC). These MHC-peptide complexes are formed intracellularly, but are ultimately presented on the plasma membrane where they serve as ligands for antigen-specific T cell receptors (TCR). In addition to TCR ligand formation, dendritic cells carry out many other functions, which allow them to control immunity at several points (Steinman, 2000).

The mechanism of CMV entry into DC has not been investigated yet. It was recently shown that DC express a lectin called DC-SIGN (DC-Specific ICAM-Grabbing Nonintegrin). DC-SIGN, also called CD209, is a ligand for IntraCellular Adhesion Molecule-2 (ICAM-2) and ICAM-3 (Geijtenbeek et al., 2000a; Geijtenbeek et al., 2000c) and is involved in the attachment of Human Immunodeficiency Virus-1 (HIV-1) (Geijtenbeek et al., 2000b) and Ebola (Alvarez et al., 2002) to DC. DC-SIGN was originally cloned from a placental cDNA library on the basis of its capacity to bind to the surface subunit HIV-1 Env glycoprotein 120 (HIV-1 gp120) (Curtis et al., 1992). DC-SIGN mediates HIV binding and internalization into DC conferring to these cells the ability to transmit HIV to permissive CD4$^+$ T cells independently from HIV-1 replication (Geijtenbeek et al., 2000b). These findings suggest that DC-SIGN efficiently captures HIV-1 at mucosal sites of inoculation and facilitates its transport to sites of infection by using the migratory ability of DC towards lymphoid organs (Banchereau and Steinman, 1998). A homologue of DC-SIGN, DC-SIGNR, was recently identified on the surface of endothelial cells and shown to display the same HIV-1 binding and trans-infection enhancement capacities shown by DC-SIGN (Bashirova et al., 2001; Pohlmann et al., 2001b). It has been suggested that the DC-SIGN lectin may act as a receptor for other glycan ligands present on other viral envelopes and on the cell walls of other microbes, or even tumor cells (Steinman, 2000). The putative role of DC-SIGN or DC-SIGNR in Herpesvirus attachment to DC or endothelial cells has never been reported.

There exists a need in the art to develop methods and compositions for modulating the specific binding of effector molecules to the DC-SIGN receptor, for example on the dendritic cells of mammals. Such methods and compositions are needed, for example, to prevent and treat diseases such as viral infections; for example CMV infections. In this regard, there is a need to identify cell proteins involved in viral attachment and/or fusion. Additionally, methods and compositions are needed that allow the specific targeting of cells expressing DC-SIGN receptor, such as dendritic cells or alveolar macrophages, to aid in therapy or diagnosis.

SUMMARY OF THE INVENTION

The inventors analyzed the mechanisms of CMV attachment to DC and the role of DC-SIGN in this process. They demonstrated that CMV is able to bind DC and DC-SIGN-expressing THP-1 cells through direct interaction of DC-SIGN with viral envelope CMV gB. Without in any way limiting the invention, the inventors believe that this binding is involved in: (1) the transmission of DC-SIGN-bound infectious viral particles to different permissive cells and (2) an enhanced infection and CMV replication in DC and DC-SIGN-expressing THP-1 cells.

Accordingly, this invention identifies DC-SIGN as a receptor involved in the binding of viruses other than HIV and Ebola virus to dendritic cells. The invention further provides a number of novel methods and compositions for treating diseases of mammals, including viral infections.

A first object of the invention is to provide a method of preventing or treating a disease of a mammal, where at least one symptom of the disease is mediated at least in part by the binding of an effector molecule to a DC-SIGN receptor of the mammal to be treated, and where the method comprises administering to the mammal an amount of a DC-SIGN modulator sufficient to substantially modulate the binding of the effector molecule to the DC-SIGN receptor to thereby prevent or treat the disease.

Another object of the invention is to provide a method of preventing or treating a disease of a mammal, where at least one symptom of the disease is mediated at least in part by the binding of an effector molecule to a DC-SIGN receptor of the mammal to be treated, and where the method comprises administering to the mammal an amount of a DC-SIGN blocker sufficient to substantially inhibit the binding of the effector molecule to the DC-SIGN receptor to thereby prevent or treat the disease.

In some embodiments the DC-SIGN blocker is a blocking derivative of the effector molecule. In other embodiments the DC-SIGN blocker is an antibody.

Among embodiments of the invention where the DC-SIGN blocker is an antibody are included embodiments where the antibody specifically binds DC-SIGN and embodiments where the antibody specifically binds the effector molecule.

In some embodiments the DC-SIGN blocker is a mannosylated molecule that binds to a DC-SIGN receptor. The mannosylated molecule may be mannan.

A further object of the invention is to provide a method of preventing or treating a viral infection of a mammal, where the viral infection is mediated at least in part by the binding of a viral effector molecule to a DC-SIGN receptor of the mammal to be treated, where the method comprises administering to the mammal an amount of a DC-SIGN modulator sufficient to substantially modulate the binding of the viral effector molecule to the DC-SIGN receptor to thereby prevent or treat the viral infection.

Another object of the invention is to provide a preventing or treating a viral infection of a mammal, where the viral infection is mediated at least in part by the binding of a viral effector molecule to a DC-SIGN receptor of the mammal to be treated, where the method comprises administering to the mammal an amount of a DC-SIGN blocker sufficient to substantially inhibit the binding of the viral effector molecule to the DC-SIGN receptor to thereby prevent or treat the viral infection.

In some embodiments of the method the DC-SIGN blocker comprises a binding moiety of the viral effector molecule. In other embodiments the DC-SIGN blocker comprises a binding moiety of a viral envelope glycoprotein. In other embodiments the DC-SIGN blocker is an antibody. The antibody may specifically bind DC-SIGN or specifically bind the viral effector molecule. In additional embodiments the DC-SIGN blocker is a mannosylated molecule that binds to a DC-SIGN receptor. The mannosylated molecule may be mannan.

Among embodiments of the invention in which the DC-SIGN blocker is an antibody are included embodiments in which the antibody is a monoclonal antibody; the mammal is a human and the antibody is a monoclonal antibody that is humanized; the antibody specifically binds DC-SIGN; the monoclonal antibody is Mab 1B10.2.6; the antibody specifically binds the viral effector molecule; and the antibody specifically binds the binding moiety of the viral effector molecule.

In further embodiments of the method the viral effector molecule is a molecular constituent of the viral envelope. In certain embodiments the molecular constituent of the viral envelope is an envelope glycoprotein.

In additional embodiments of the method the DC-SIGN blocker comprises a binding moiety of the viral effector molecule. In some embodiments of the invention in which the viral effector molecule is a molecular constituent of the viral envelope the DC-SIGN blocker that is used comprises a binding moiety of the envelope glycoprotein.

In a preferred aspect of the invention the viral infection is a CMV infection and the viral effector molecule is a CMV effector molecule. In a further preferred aspect the mammal is a human. In some embodiments the CMV effector molecule is a molecular constituent of the CMV envelope. In further embodiments the molecular constituent of the CMV envelope is a CMV envelope glycoprotein. In yet further embodiments the CMV envelope glycoprotein is CMV envelope glycoprotein B.

Included among embodiments of the invention in which the viral infection is a CMV infection and the viral effector molecule is a CMV effector molecule are embodiments where the DC-SIGN blocker comprises a binding moiety of the CMV effector molecule; the DC-SIGN blocker comprises a binding moiety of the CMV envelope glycoprotein B; the DC-SIGN blocker is a recombinantly produced protein; and the DC-SIGN blocker is an antibody. Among embodiments where the DC-SIGN blocker is an antibody are embodiments where the antibody is a monoclonal antibody; the mammal is a human and the monoclonal antibody is humanized; the antibody specifically binds DC-SIGN; the monoclonal antibody is Mab 1B10.2.6; and the antibody specifically binds the CMV effector molecule. Among embodiments where the antibody specifically binds the CMV effector molecule are embodiments where the CMV effector molecule is CMV envelope glycoprotein B.

In a further aspect the invention provides a method of preventing or treating an Ebola, HIV or SIV infection of a human or a simian, where the method comprises administering to the human or simian an amount of a DC-SIGN modulator sufficient to substantially modulate the binding of HIV or SIV to the DC-SIGN receptor present on dendritic cells of the human or simian to thereby prevent or treat the HIV or SIV infection.

In another aspect the invention provides a method of preventing or treating an Ebola, HIV or SIV infection of a human or a simian, where the method comprises administering to the human or simian an amount of a DC-SIGN blocker sufficient to substantially inhibit the binding of HIV or SIV to the DC-SIGN receptor present on dendritic cells of the human or simian to thereby prevent or treat the HIV or SIV infection. In a preferred embodiment the DC-SIGN blocker comprises a binding moiety of the CMV envelope glycoprotein B. In another preferred embodiment an HIV infection of a human is prevented or treated.

In a further aspect the invention provides a method of preventing or treating an Ebola, HIV or SIV infection of a human or a simian, where the method comprises administering to the human or simian an amount of a DC-SIGN modulator sufficient to substantially modulate the binding of HIV or SIV to the DC-SIGN receptor present on dendritic cells of the human or simian to thereby prevent or treat the HIV or SIV infection.

In another aspect the invention provides a method of preventing or treating an Ebola, HIV or SIV infection of a human or a simian, where the method comprises administering to the human or simian an amount of a DC-SIGN blocker sufficient to substantially inhibit the binding of HIV or SIV to the DC-SIGN receptor present on dendritic cells of the human or simian to thereby prevent or treat the HIV or SIV infection. In a preferred embodiment the DC-SIGN blocker comprises a binding moiety of the CMV envelope glycoprotein B. In another preferred embodiment an HIV infection of a human is prevented or treated.

In a further aspect the invention provides a pharmaceutical composition comprising:
　a) A DC-SIGN modulator, and
　b) at least one pharmaceutically acceptable excipient;
　　wherein the DC-SIGN blocker is present in the composition at an achievable therapeutic concentration.

In a further aspect the invention provides a pharmaceutical composition comprising:
　c) A DC-SIGN blocker, and
　d) at least one pharmaceutically acceptable excipient;
　　wherein the DC-SIGN blocker is present in the composition at an achievable therapeutic concentration.

In some embodiments of the pharmaceutical composition the DC-SIGN blocker is a derivative of a viral effector molecule. In one embodiment DC-SIGN blocker comprises the binding moiety of a CMV effector molecule. In another embodiment the CMV effector molecule is CMV envelope glycoprotein B.

In other embodiments of the pharmaceutical composition the DC-SIGN blocker is an antibody. Embodiments where the DC-SIGN blocker is an antibody include embodiments where the antibody is a monoclonal antibody; the monoclonal antibody is humanized; the antibody specifically binds DC-SIGN; the monoclonal antibody is Mab 1B10.2.6; the antibody specifically binds the viral effector molecule; or the antibody specifically binds the binding moiety of the viral effector molecule.

In a further aspect the invention provides a method of identifying a DC-SIGN modulator, wherein the method comprises:
　a) determining a baseline binding value by:
　　i. providing cultured cells comprising a DC-SIGN receptor;
　　ii. exposing the cultured cells to a marked viral effector molecule binding moiety for a period of time sufficient to allow binding equilibrium to be reached; and
　　iii. determining the extent of binding of the marked viral effector molecule binding moiety to the cultured cells to thereby determine a baseline binding value;
　b) determining a test substance binding value by:
　　i. providing cultured cells comprising a DC-SIGN receptor;
　　ii. exposing the cultured cells to a marked viral effector molecule binding moiety in the presence of a test substance for a period of time sufficient to allow binding equilibrium to be reached; and
　　iii. determining the extent of binding of the marked viral effector molecule binding moiety to the cultured cells to thereby determine a test substance binding value; and
　c) determining a test substance binding modulation value for the test substance by dividing the test substance binding value by the baseline binding value,
　wherein a test substance binding inhibition value representing an about 95% modulation of binding of the viral effector molecule to dendritic cells by the test substance, indicates that the test substance is a substance that substantially modulates the binding of a viral effector molecule to the DC-SIGN receptor.

In a preferred aspect the invention provides a method of identifying a DC-SIGN blocker, wherein the method comprises:
　a) determining a baseline binding value by:
　　i. providing cultured cells comprising a DC-SIGN receptor;
　　ii. exposing the cultured cells to a marked viral effector molecule binding moiety for a period of time sufficient to allow binding equilibrium to be reached; and
　　iii. determining the extent of binding of the marked viral effector molecule binding moiety to the cultured cells to thereby determine a baseline binding value;
　b) determining a test substance binding value by:
　　i. providing cultured cells comprising a DC-SIGN receptor;
　　ii. exposing the cultured cells to a marked viral effector molecule binding moiety in the presence of a test substance for a period of time sufficient to allow binding equilibrium to be reached; and
　　iii. determining the extent of binding of the marked viral effector molecule binding moiety to the cultured cells to thereby determine a test substance binding value; and
　c) determining a test substance binding inhibition value for the test substance by dividing the test substance binding value by the baseline binding value,
　wherein a test substance binding inhibition value representing an about 95% inhibition of binding of the viral effector molecule to dendritic cells by the test substance, indicates that the test substance is a substance that substantially inhibits the binding of a viral effector molecule to the DC-SIGN receptor.

The method of identifying a DC-SIGN blocker includes embodiments where the cultured cells are DC; the cultured cells are THP-1 cells; the viral effector molecule is a CMV effector molecule; and the CMV effector molecule is CMV envelope glycoprotein B.

In a further aspect the invention provides an isolated DC-SIGN blocker identified by the above method of identifying a DC-SIGN blocker.

In another aspect the invention provides a method of targeting a subject molecule to a cell expressing a DC-SIGN receptor by exposing the cell to a targeting complex, where the targeting complex comprises a subject molecule and a DC-SIGN blocker, and where the exposure is under conditions which allow the DC-SIGN blocker to bind to DC-SIGN on the cell expressing the DC-SIGN receptor, thereby targeting the subject molecule to the cell expressing a DC-SIGN receptor.

The method of targeting a subject molecule to a cell expressing a DC-SIGN receptor includes embodiments where the DC-SIGN blocker is an antibody; the DC-SIGN blocker is a monoclonal antibody; the subject molecule is a protein; the subject molecule is an antibody; the subject molecule is labeled; the exposure occurs in vivo; and the exposure occurs in vitro.

In a further aspect the invention provides an isolated antibody, wherein the isolated antibody specifically binds DC-SIGN. In one embodiment, the antibody is a DC-SIGN modulator. In a preferred embodiment, the antibody is a DC-SIGN blocker. In a further embodiment, the invention provides an isolated monoclonal antibody, wherein the isolated monoclonal antibody specifically binds DC-SIGN. In one embodiment the monoclonal antibody is a DC-SIGN modulator. In a preferred embodiment, the monoclonal antibody is a DC-SIGN blocker. In the further preferred embodiment, the isolated monoclonal antibody is Mab 1B10.2.6, produced by hybridoma 1B10.2.6, deposited at the C.N.C.M. on Nov. 7, 2002, under the accession number I-2951.

The address of the Collection Nationale De Cultures De Micro-organismes (CNCM) is Institut Pasteur, 28, rue du Dr Roux, 75724 Paris Cédex 15, France.

BRIEF DESCRIPTION OF THE DRAWINGS

The invention will be more fully described with reference to the drawings in which:

FIG. 1 shows that DC-SIGN-expressing cells bind CMV on their surface. (A) Detection of DC-SIGN. Anti-DC-SIGN 1B10.2.6 mAb (bold line). Irrelevant isotypic control mAb (dotted line). Mean fluorescence intensity (MFI) values are indicated. (B) Binding of CMV AD169 strain to cells expressing or not DC-SIGN was revealed by an anti-envelope glycoprotein B (CMV gB) mAb. Incubation in low pH buffer (200 PFU/cell) prior to staining abrogates detection of CMV gB.

FIG. 2 depicts DC-SIGN-dependent trans-infection of CMV permissive cells. (A) MD-DC, (B) DC-SIGN$^+$ vs parental THP-1 cells or (C) parental vs DC-SIGN$^+$ HeLa cells were pre-treated with EGTA (5 mM), mannan (20, 1, 0.05 μg/ml), anti-DC-SIGN 1B10.2.6 mAb (20, 1, 0.05 μg/ml) or an isotypic control (20, 1, 0.05 μg/ml) prior to incubation with ADGFP strain (1 PFU/cell). After removal of unbound virus and competitors, ADGFP-challenged cells were co-cultured for 3 days with MRC-5 cells. Infection of MRC-5 was assessed by counting the number of GFP-expressing cells by flow cytometry.

FIG. 3 shows that DC-SIGN enhances CMV trans-infection of MRC-5 cells and retains long term infectious virus. (A) MD-DC, (B) parental or DC-SIGN$^+$ THP-1 cells, were incubated with ADGFP in the absence or in the presence either of anti-DC-SIGN 1B10.2.6 mAb or an isotypic, control mAB. Thereafter, cells were co-cultured with reporter MRC-5 cells. (C) DC-SIGN$^+$ and parental THP-1 cells were incubated (4 hours) with ADGFP (MOI=1) and washed thereafter. At days 0, 2, 4, 6, 8 after pulse, ADGFP-challenged cells were co-cultured with reporter MRC-5 cells for 3 days. In (A), (B) and (C), MRC-5 cells were incubated with the corresponding amount of cell-free virus to monitor kinetic and extent of infection. Values represent the percentage of MRC-5 cells expressing GFP.

FIG. 4 Shows that DC-SIGN mediates CMV transmission to different permissive cells but does not allow transmission of HSV-1 and VZV. (A) and (B), DC-SIGN$^+$ THP-1 cells were exposed either to anti-DC-SIGN 1B10.2.6 mAb or an isotypic control mAb prior to infection with ADGFP. ADGFP-pulsed DC-SIGN$^+$ THP-1 cells were co-cultured for 24 hours either with MRC-5 (A) or U373 MG cells (B). GFP- (grey bars) or CMV IEA/EA-expressing cells (open bars) were counted to evaluate CMV infection. (C) DC-SIGN$^+$ THP-1 cells incubated with anti-DC-SIGN 1B10.2.6 mAb (open bars), an isotypic control mAb (dashed bars) or left untreated (grey bars) were exposed for 1 hr to TB40/E, AD169 or Towne CMV isolates, HSV-1 or VZV. After removal of unbound virus and mAb, cells were co-cultured with MRC-5 reporter cell line for 5 days. (D) MRC-5 cells were exposed for 5 days to identical amount of cell-free viruses as used in C to infect DC-SIGN$^+$ THP-1 cells. IEA/EA-expressing cells were detected by immunocytochemistry using specific antibodies for each herpesvirus.

FIG. 5 Shows that the DC-SIGN cytoplasmic domain is required for CMV transmission. (A) Cell surface expression of wt or mutated DC-SIGN (Δ35 and Δ20) receptors analyzed by immunostaining (1B10.2.6 mAb) and flow cytometry. (B) CMV-binding capacity of THP-1 expressing wt or truncated DC-SIGN revealed by anti-CMV gB mAb. (C) Parental, or DC-SIGN$^+$ cells were incubated, either at 4° C. or at 37° C. for 2 hours, with ADGFP CMV (MOI=0.1) and co-cultured with MRC-5 cells for 3 days. Infection was assessed by estimating the number of GFP-expressing cells.

FIG. 6 Shows that DC-SIGN expression renders susceptible cells permissive to CMV infection. A) Cells were pre-treated for 30 min with medium (grey bars), anti-DC-SIGN 1B10.2.6 mAb (open bars) or an isotypic control mAb (dashed bars) and thereafter incubated with ADGFP strain (1 PFU/cell). HEK 293T were transiently transfected either with a DC-SIGN cDNA plasmid or a control plasmid (pcDNA3.1). (B) HEK 293T cells were transiently transduced with DC-SIGN or DC-SIGNR cDNAs and incubated with ADGFP. In (A) and (B), GFP-expressing cells were quantified by flow cytometry at 3 day after infection. (C) THP-1, DC-SIGN$^+$ THP-1 cells or MD-DC were pre-treated as described in (A) (same symbols) and infected with TB40/E CMV (MOI=1) for 3 days. CMV infection was assessed by immunostaining with specific CMV IEA/EA mAb. Total number of CMV IEA/EA-positive cells on the slide was determined by extrapolating the number of positive cells contained in the optical field of the microscope (×10 objective). (D) MD-DC, MRC-5, parental and DC-SIGN$^+$ THP-1 cells were pre-treated and infected as described in (C). Non-internalized viral particles were removed by short incubation in a low pH buffer. At day 14 after infection virions released in culture supernatants, were titrated on MRC-5 cells by plaque assays. Figures on top of histograms indicate infection fold amplification which result from dividing the absolute number of CMV particles collected in supernatants by the absolute number of CMV particles used to infect cells (20,000 PFU).

FIG. 7 depicts data that identify CMV gB as a viral ligand for DC-SIGN and characterization of the DC-SIGN/CMV gB interaction by SPR. (A) Binding of CMV gB to DC-SIGN. DC-SIGN$^+$ THP-1 cells or MD-DC were pre-treated with medium (black closed circles), anti-DC-SIGN 1B10.2.6 mAb (open circles) or an isotypic, control mAb (grey closed circles), and thereafter incubated with biotinylated CMV gB. Cell-bound CMV gB was revealed by PE-labelled streptavidin. Incubation of parental THP-1 cells with biotinylated CMV gB is also shown (black closed triangles). (B) Competition assay of biotinylated HIV-1 gp120 binding to DC-SIGN. Parental (upper panel) or DC-SIGN$^+$ THP-1 cells (all other panels) were incubated with 2 Pg/mL of biotinylated HIV-1 gp120. DC-SIGN+ THP-1 cells were left untreated or pre-incubated with potential competitors (unlabelled HIV-1 gp120, mannan, anti-DC-SIGN 1B10.2.6 mAb, control isotypic mAb, or envelope glycoproteins from CMV gB, HSV-1 gB and gD or VZV gE and gB) before incubation with biotinylated HIV-1 gp120. MFI of biotinylated HIV-1 gp120 staining is indicated in the upper-right corner of histograms. In each panel, control staining (dotted line), biotinylated HIV-1 gp120 labelling in the absence of competitor (gray-filled profile) or after pre-incubation with competitors (black-filled histogram), are shown. (C) Binding of CMV gB to DC-SIGNR. HEK 293T cells were transiently transfected either with a control plasmid or plasmids encoding DC-SIGN or DC-SIGNR cDNAs. Transfected cells were incubated with increasing concentrations of biotinylated-CMV gB (dashed bars), biotinylated-HIV-1 gp120 (black bars) or biotinylated-BSA (open bars). Binding of biotinylated proteins was revealed by PE-conjugated streptavidin and analyzed by flow cytometry. Values are represented as MFI. (D) SPR analysis of DC-SIGN/CMV gB interaction. The recombinant soluble CRD of DC-SIGN at (from bottom to top) 0.13, 0.21, 0.36, 0.6 or 1 µM was injected over surfaces coated with HIV-1 gp120 (left panel), CMV gB (middle panel) or HSV-1 gB (right panel) to analyze the association phase, after which running, buffer alone was injected to analyze the dissociation phase. Binding responses (Response Unit, RU) are reported as a function of time. Dissociation constants (Kd) are indicated for left and middle panels.

DETAILED DESCRIPTION OF THE INVENTION

This invention relates to a method of preventing or treating a disease of a mammal, where at least one symptom of the disease is mediated at least in part by the binding of an effector molecule to a DC-SIGN receptor of the mammal to be treated. The method comprises administering to the mammal an amount of a DC-SIGN blocker sufficient to substantially inhibit the binding of the effector molecule to the DC-SIGN receptor to thereby prevent or treat the disease.

"Mammal" for purposes of the invention refers to any animal classified within the class mammalia. Nonlimiting examples of mammals include: humans and simians; pet animals, such as dogs, cats, ferrets, and guinea pigs; farm animals, such as pigs, cows, horses, sheep, goats, and llamas; and zoo animals, such as bears, zebras, elephants, and water buffalo. The mammal is preferably human.

As used herein a "disease" is any pathological condition of a mammal, which results, for example, from infection, genetic defect, or exposure to a substance in the environment. The methods and compositions of the invention are useful for preventing or treating diseases that are characterized in that at least one symptom of the disease is mediated at least in part by the binding of an effector molecule to the DC-SIGN receptor present on cells such as dendritic cells or alveolar macrophages of the mammal. Specific examples of such diseases include viral infection. A specific examples of viral infections that can be treated by the method is CMV infection of a human.

In the case of humans "DC-Specific ICAM-Grabbing Nonintegrin receptor" or "DC-SIGN receptor" refers generically to DC-SIGN (described in Curtis et al., 1992) and/or DC-SIGNR (described in Pohlmann et al., 2001), and/or a homologue of DC-SIGN or DC-SIGNR. One of skill in the art will recognize that there may be some situations in which use of one or the other of these forms of DC-SIGN receptor is preferable or even necessary. One of skill in the art will recognize that human DC-SIGN protein can be obtained from many sources. For example, human DC-SIGN can be purified from human dendritic cells which are obtained from an in vivo source, such as human blood, or purified from an in vitro source, such as human dendritic cells produced in tissue culture from human dendritic cell precursor cells. It is also possible to express human DC-SIGN using a recombinant system, using either cultured dendritic cell as a host or a suitable heterologous cell type, such as COS-7 or HeLa cells, or bacteria such as E. coli.

In the case of nonhuman mammals, "DC-SIGN receptor" refers to homologues of a human DC-SIGN receptor. One of skill in the art will recognize that such proteins may be identified in any of a number of different ways. These include expression cloning, polymerase chain reaction using degenerate oligonucleotide primers, and low stringency screening of a bacterial or bacteriophage library.

Dendritic cells are a diverse population of morphologically similar cell types found in lymphoid or non-lymphoid tissues. Dendritic cells function as antigen-presenting cells that efficiently capture antigens in the peripheral tissues and process them to form MHC-peptide complexes. Dendritic cells are also involved in the early activation of non-MHC-restricted γδ and CDI-restricted T cells specific for various mycobacterial glycolipids, including CAM (Kaufmann, 2001 and Moody, et al., 2000). After antigen uptake, these immature dendritic cells acquire the unique capacity to migrate from the periphery to the T cell areas of the secondary lymphoid organs. Dendritic cells convert antigens from foreign cells and infectious microorganisms into short peptides that are bound to membrane proteins of the major histocompatibility complex (MHC). These MHC-peptide complexes are formed intracellularly but are ultimately presented on the plasma membrane where they serve as ligands for antigen-specific T cell receptors (TCR). In addition to TCR ligand formation, dendritic cells carry out many other functions, which allow them to control immunity at several points (Steinman, 2000).

Alveolar macrophages and dendritic cells are examples of cells expressing a DC-SIGN receptor. Endothelial cells are an example of cells expressing DC-SIGNR.

One of skill in the art will appreciate that dendritic cells may be obtained from an in vivo source, such as the blood of a mammal, or grown in vitro, by culturing dendritic cell precursor cells under appropriate conditions. Dendritic cell precursor cells include monocytes prepared according to Example 3.

An "effector molecule" is any molecule that specifically binds to the DC-SIGN receptor present on cells of a mammal, such as the dendritic cells or the alveolar macrophages of a mammal, and thereby mediates a symptom that is associated with a disease of that mammal. Examples of effector molecules are ligands present on viruses that bind to receptors on cells of a mammal and thereby facilitate the entry of the virus into a cell of the mammal. In cases where the effector molecules are ligands present on viruses the effector molecules can be referred to as "viral effector molecules." Examples of this type of ligand include gp120 of HIV and envelope glycoprotein B of CMV, which bind with the DC-SIGN receptor present on cells such as dendritic cells or alveolar macrophages of a human to facilitate, in the case of CMV, the transmission of DC-SIGN-bound infectious viral particles to different permissive cells and an enhanced infection and CMV replication in DC and DC-SIGN-expressing THP-1 cells. CMV envelope glycoprotein B is thus a "CMV effector molecule." Other types of effector molecules are ligands that are endogenous to the mammal. This type of ligand includes both ligands that are bound to the surface of other cells of the mammal and soluble ligands, which may be localized to the extracellular space of a particular tissue or circulating systemically.

A "symptom" is any pathological manifestation of the disease to be treated. A symptom is caused at least in part by the binding of an effector molecule to the DC-SIGN receptor present on the dendritic cells of the mammal to be treated if a modulation (a reduction or an increase) in the binding of the effector molecule to the DC-SIGN receptor causes a determinable reduction in the occurrence or severity of the symptom, or both. In a preferred embodiment of the invention the symptom is no longer present or is prevented from occurring following the reduction in the binding of the effector molecule to the DC-SIGN receptor.

An effector molecule is said to "specifically bind" to the DC-SIGN receptor present on cells such as the dendritic cells or the alveolar macrophages of the mammal to be treated if such binding is not competitively inhibited by the presence of unrelated molecules (e.g., fetal calf serum), but is inhibited by antibodies to DC-SIGN (e.g., 1B10.2.6) and/or additional effector molecule.

An example of an effector molecule that specifically binds to the DC-SIGN receptor present on cells such as the dendritic cells or the alveolar macrophages of a mammal to be treated is CMV envelope glycoprotein B.

One of skill in the art will appreciate that these assays may be used to identify other effector molecules that specifically bind to the DC-SIGN receptor present on cells such as dendritic cells of a mammal to be treated. It will also be clear to one of skill in the art that other equivalent assays may be substituted for those specifically disclosed in the Examples.

Once an effector molecule is known to specifically bind to the DC-SIGN receptor the binding of the effector molecule to DC-SIGN can be referred to simply as "binding." It will be understood by one of skill in the art that such binding is specific. In this regard, the "modulation" of binding may be discussed. Modulation can include "inhibition" or "enhancement".

"Modulation" means the act of regulating. It includes the act of inducing variations of a property of a molecule. In the context of the present invention, "modulation" means the act of regulating and varying the binding of effector molecules to their receptors. This modulation may serve to either inhibit or enhance binding, or to impose other regulatory controls.

In the context of the present invention "inhibition" of binding means a reduction in the total amount of effector molecule that binds to DC-SIGN over a fixed period of time. Inhibition of binding of the effector molecule is achieved by providing a DC-SIGN blocker. A "DC-SIGN blocker" is any molecule that substantially inhibits the binding of a given effector molecule at a concentration at which the effector molecule specifically binds to DC-SIGN. In a preferred embodiment, the DC-SIGN blocker used is a monoclonal antibody that specifically binds DC-SIGN. In another preferred embodiment the DC-SIGN blocker used comprises a binding moiety of the CMV envelope glycoprotein B.

In the context of the present invention "enhancement" of binding means an increase in the total amount of effector molecule that binds to DC-SIGN over a fixed period of time. Enhancement of binding of the effector molecule is achieved by providing a DC-SIGN enhancer. A "DC-SIGN enhancer" is any molecule that substantially enhances the binding of a given effector molecule at a concentration at which the effector molecule specifically binds to DC-SIGN.

A "binding moiety" is that portion of a molecule that substantially retains the ability to bind to a second molecule when other portions of the molecule are removed or modified or when the binding moiety is placed into a heterologous context. For example, in the case of an effector molecule as defined herein, a binding moiety of the effector molecule can be defined. A binding moiety of an effector molecule is that portion of the effector molecule that substantially retains the ability to bind to DC-SIGN when other portions of the molecule are removed or modified or when the binding moiety is placed into a heterologous context. In this context, "substantially retains" can be defined by one of skill based on the specific properties of the binding moiety that are sought.

"Substantially inhibit" means greater than 80% inhibition, greater than 90% inhibition, greater than 95% inhibition, or greater than 99% inhibition. In a preferred embodiment of the present invention about 90% binding inhibition is obtained.

"Inhibition" is measured by comparing the extent of effector molecule binding to DC-SIGN in the presence of a DC-SIGN blocker with the extent of effector molecule binding to DC-SIGN in the absence of a DC-SIGN blocker. The ratio of extent of binding in the presence of the DC-SIGN blocker compared to the extent of binding in the absence of the DC-SING blocker is then determined. The percent inhibition is then the proportional reduction in the amount of binding. For example, a ratio of 0.1 represents a 90% reduction in binding.

The term "treat," "treating" or "treatment" refers to the administration of therapy to an individual who already manifests at least one symptom of a disease. Such an individual includes an individual who is diagnosed as having a known disease.

The term "prevent," "preventing" and "prevent" refers to the administration of therapy on a prophylactic or preventative basis to an individual who may ultimately acquire the disease but who has not yet done so (i.e., those needing preventative measures). Such individuals may be identified on the basis of risk factors that are known to correlate with the subsequent occurrence of the disease.

The term "therapeutic benefit" refers to an improvement of at least one symptom of a disease, a slowing of the progression of a disease, as manifested by a slowing in the increase in severity of at least one symptom of a disease, or a cessation in the progression of at least one symptom of a disease. The therapeutic benefit is determined by comparing a symptom of a disease before and after a DC-SIGN blocker is administered.

The term "antibody" refers to any antibody that can be made by any technique known in the art. Suitable antibodies are obtained by immunizing a host animal with peptides comprising all or a portion of the target protein. Suitable host animals include mouse, rat sheep, goat, hamster, rabbit, etc. The origin of the protein immunogen may be mouse, human, rat, monkey, etc or a microorganism, including a bacteria or a virus. The host animal will generally be a different species than the immunogen, e.g. human protein used to immunize mice, etc.

The immunogen may comprise the complete protein, or fragments and derivatives thereof. Preferred immunogens comprise all or a part of one of the subject proteins, where these residues contain the post-translation modifications, such as glycosylation, found on the native target protein. Immunogens comprising the extracellular domain are produced in a variety of ways known in the art, e.g. expression of cloned genes using conventional recombinant methods, isolation from tumor cell culture supernatants, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against a mouse protein, the animal will generally be a hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also provided are "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies which are identical to human antibodies may be employed. By xenogenic human antibodies is meant antibodies that are the same has human antibodies, i.e. they are fully human antibodies, with exception that they are produced using a non-human host which has been genetically engineered to express human antibodies. See e.g. WO 98/50433; WO 98,24893 and WO 99/53049, the disclosures of which are herein incorporated by reference.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc An example of a disease that can be prevented or treated utilizing the present invention is CMV infection. The results presented in the examples demonstrate for the first time a role for DC-SIGN in CMV binding to human dendritic cells.

The experiment described herein, including the results described in the examples, provide new insights into the mechanisms of interaction of CMV with DC and the transmission of CMV infection to other cell targets. The data show that DC-SIGN accounts for most of the binding of CMV to DC and mediates the attachment of CMV virions when expressed in DC-SIGN negative cells. Interaction of CMV with DC-SIGN occurs through specific binding with at least one CMV envelope glycoprotein, CMV gB. DC-SIGN is a type II membrane protein in which the extracellular domain encompass the CRD and a stalk that mediates tetramerization (Mitchell et al., 2001). Like DC-SIGN, CMV gB is also present in multimeric complexes in CMV envelope (Scheffczik et al., 2001). CMV gB-DC-SIGN interactions analysed by SPR were conducted using recombinant soluble forms of DC-SIGN CRD, which are monomers. The affinity of CMV gB for DC-SIGN measured by SPR was 0.3 PM and was comparable to that estimated for HIV-1 gp120 (Mitchell et al., 2001). This relatively low affinity is likely due to the inability of CRD to multimerize. The estimated affinity (Kd) of HIV-1 gp120 for the natural DC-SIGN molecule is 1.4 nM (versus 5 nM for CD4) (Curtis et al., 1992). These findings suggest that, like HIV-1 gp120, CMV gB would display high affinity for oligomerized DC-SIGN.

DC-SIGN-bound CMV retains infectious capacity since, upon binding onto DC-SIGN$^+$ THP-1 cells or MD-DC, CMV is transmitted to permissive cells where the virus replicates actively. DC are receptive to CMV infection by primary, non-adapted CMV isolates and refractory to infection by adapted, CMV laboratory strains. The capacity of DC to transmit CMV to permissive cell targets can be dissociated from the ability of CMV to infect and replicate in DC. This result was confirmed using DC-SIGN$^+$ HeLa cells which were capable of transmitting CMV to permissive target cells while CMV IE antigen expression was never detected in these refractory cells. This DC-SIGN function is reminiscent of the aptitude to transmit infection to CD4$^+$ T lymphocytes shown either by HIV-1-pulsed-DC or -DC-SIGN-transduced cells.

Binding to, and transfer of HIV-1 from, DC-SIGN$^+$ cells appear to be separable steps (Pohlmann et al., 2001a). Recently, it has been shown that efficient transmission of HIV to CD4$^+$ T lymphocytes from DC-SIGN-expressing THP-1 cells requires internalization signals encoded in the cytoplasmic domain of the lectin (Kwon et al., 2002). The requirement of DC-SIGN cytoplasmic signals for efficient trans-infection (named trans-enhancement) becomes particularly evident when low amount of virus are used as inoculum (Geijtenbeek et al., 2000b). Similarly to HIV, sub-optimal inoculums of CMV become highly infectious when transferred from DC-SIGN$^+$ THP-1 cells. Moreover, DC-SIGN $\Delta$35 and $\Delta$20 failed to support CMV transmission to highly susceptible cells and incubation of CMV with wild type- or truncated-DC-SIGN-expressing cells at 4° C. prevented CMV transmission to permissive cells. These findings suggest that endocytosis of the receptor is required for efficient transmission of CMV to permissive cells. However, the experiments reported here do not permit to rule out the involvement of putative transduction of intracellular signals in this phenomenon since deletion of DC-SIGN cytoplasmic domains or inhibition of cell signal activation at 4° C. may preclude DC-SIGN-dependent cell activation. Overall, these findings suggest that in the natural CMV infection, DC-SIGN promotes take up of CMV and permits enhancement of CMV transmission by interstitial DC to other cells. The hypothesis of in vivo CMV transport by DC raised the question of the stability of DC-SIGN-bound CMV particles. As previously described for HIV, the experiments described herein provide evidence that DC-SIGN$^+$ THP-1 cells can transmit CMV to other cell targets after five days in culture whereas cell-free virus loss infectivity upon incubation at 37° C. for 24 to 48 hours. The ability of DC to transmit infection long time after exposure supports the hypothesis that DC transport small amounts of CMV from entry sites to target organs where they could transmit infectious CMV particles by cell-to-cell contact.

A striking feature of DC-SIGN-CMV interactions is the capacity of the lectin to facilitate the infection of low-susceptible cells to CMV infection. Thus, THP-1 cells that do not normally support CMV replication become productively infected as they express DC-SIGN. CMV attachment to host cells is supposed to occur namely through low affinity interactions with heparan sulfate proteoglycans (Compton et al., 1993; Kari and Gehrz, 1992). However, beyond this primary site of binding, the existence of an alternative cellular co-factor, required for a strong attachment of CMV on cell membranes as well as for its entry into cells, is postulated (Boyle and Compton, 1998). Annexin II, which binds to CMV gB (Pietropaolo and Compton, 1997) and a 92.5 kDa protein which binds to CMV gH (Baldwin et al., 2000), have been proposed to play this role. It is unlikely that DC-SIGN is the elusive CMV receptor that ultimately determines entry of the enveloped virions and replication in CMV-infection susceptible cells. Indeed, CMV entry and infection occurs in a number of cell types (i.e., MRC-5 fibroblasts and U373 MG astrocytoma cells) where DC-SIGN is not expressed. The putative CMV receptor in these cells might be different from a lectin, although the existence of yet unidentified DC-SIGN-like molecules accounting for binding and entry of CMV cannot be formally ruled out.

The capacity of DC-SIGN to promote in cis CMV replication in otherwise low-susceptible cells may result from any of three not mutually exclusive hypotheses. DC-SIGN has the capacity to capture and internalize HIV-1 in DC (Kwon et al., 2002). By analogy, DC-SIGN might promote internalization and trafficking of CMV to an intracellular compartment from where it could initiate the infectious cycle. Alternatively, attachment of CMV to DC-SIGN, or DC-SIGNR, might facilitate the interaction with the authentic cellular receptor, which ultimately would account for CMV entry. Such a function would be reminiscent of the facilitating effect shown by DC-SIGN on HIV infection of T lymphocytes displaying low levels of CCR5 (Lee et al., 2001). Finally, differentiation of THP-1 cells with TPA was shown to induce permissiveness to CMV replication (Weinshenker et al., 1988). Similarly, signal transduction through DC-SIGN could lead to cellular differentiation and subsequent CMV replication.

Regarding CMV infection, the in cis capacity of DC-SIGN to facilitate viral entry is likely of biological relevance since the blockade by specific anti-DC-SIGN antibodies drastically reduces infectiveness of DC by primary, CMV isolates. The capacity of DC to support CMV infection may be related to the amount of DC-SIGN expressed at their surface. Thus, immature DC which express high levels of DC-SIGN can be infected by CMV (Raftery et al., 2001; Riegler et al., 2000) while matured DC that display low DC-SIGN expression show reduced susceptibility to CMV. Expression of DC-SIGN on immature DC of intestinal and genital mucosae (Geijtenbeek et al., 2000b; Jameson et al., 2002) may confer to this co-factor a crucial role for the infection of these primary target cells at the anatomical sites where initial CMV transmission or propagation most probably take place. A recent study described a monocyte-derived macrophage circulating subset, expressing DC markers in vivo (Soderberg-Naucler et al., 1997). This subset was shown to harbor latent CMV which reactivates upon allogeneic stimulation. It appears necessary to investigate the expression of DC-SIGN by these cells which could represent a biological link between this newly identified dendritic-like subset and the results described herein. As recently reported, CMV infected DC display decreased antigen presentation and differentiation capacities (Andrews et al., 2001; Raftery et al., 2001). Hence, by promoting DC mediated trans-infection of target cells as well as cis-infection of DC, DC-SIGN could be involved, apart from virus propagation, in CMV-mediated altered immune response.

The data reported herein show that DC-SIGNR is also able to bind CMV gB and to promote cis-infection of apparently low susceptible cells. This DC-SIGN homologue is mainly expressed on EC (Bashirova et al., 2001; Pohlmann et al., 2001b) which are known to be preferential targets of CMV in vivo and replicate primary, non-adapted CMV strains in vitro (Kahl et al., 2000). The expression of DC-SIGNR on placental EC and macrophages (Soilleux et al., 2001) could be involved in the materno-fetal transmission of CMV during congenital infections. Similarly, DC-SIGNR expressed in liver EC may be implicated in CMV-induced hepatitis, one of the most frequent clinical forms of this infection.

Murine CMV shares many essential characteristics with its human counterpart and has been a widely studied model for CMV infection. It has been shown that infection of DC by murine CMV prevents delivery of the signals required for T cell activation. The impairment of DC functions by murine CMV is supposed to be detrimental for the host immune responses (Andrews et al., 2001). The cloning of several homologues of DC-SIGN in mice (Park et al., 2001), should provide this model with an invaluable tool for studying the implication of DC-SIGN-like molecules in the dynamic of CMV dissemination, the role of the different subsets of DC in the course of CMV propagation and eventually the causes of CMV-induced immunosuppression.

In accordance with these results, the invention provides a method of preventing or treating a disease of a mammal, where at least one symptom of the disease is mediated at least in part by the binding of an effector molecule to a DC-SIGN receptor of the mammal to be treated, and where the method comprises administering to the mammal an amount of a DC-SIGN blocker sufficient to substantially inhibit the binding of the effector molecule to the DC-SIGN receptor to thereby prevent or treat the disease.

In some embodiments the DC-SIGN blocker is a blocking derivative of the effector molecule. In other embodiments the DC-SIGN blocker is an antibody.

Among embodiments of the invention where the DC-SIGN blocker is an antibody are included embodiments where the antibody specifically binds DC-SIGN and embodiments where the antibody specifically binds the effector molecule.

In some embodiments the DC-SIGN blocker is a mannosylated molecule that binds to a DC-SIGN receptor. The mannosylated molecule may be mannan.

The invention also provides a method of preventing or treating a viral infection of a mammal, where the viral infection is mediated at least in part by the binding of a viral effector molecule to a DC-SIGN receptor of the mammal to be treated, where the method comprises administering to the mammal an amount of a DC-SIGN blocker sufficient to substantially inhibit the binding of the viral effector molecule to the DC-SIGN receptor to thereby prevent or treat the viral infection.

In some embodiments of the method the DC-SIGN blocker comprises a binding moiety of the viral effector molecule. In other embodiments the DC-SIGN blocker comprises a binding moiety of a viral envelope glycoprotein. In other embodiments the DC-SIGN blocker is an antibody. The antibody may specifically bind DC-SIGN or specifically bind the viral effector molecule. In additional embodiments the DC-SIGN blocker is a mannosylated molecule that binds to a DC-SIGN receptor. The mannosylated molecule may be mannan.

Among embodiments of the invention in which the DC-SIGN blocker is an antibody are included embodiments in which the antibody is a monoclonal antibody; the mammal is a human and the antibody is a monoclonal antibody that is humanized; the antibody specifically binds DC-SIGN; the monoclonal antibody is Mab 1B10.2.6; the antibody specifically binds the viral effector molecule; and the antibody specifically binds the binding moiety of the viral effector molecule.

In further embodiments of the method the viral effector molecule is a molecular constituent of the viral envelope. In certain embodiments the molecular constituent of the viral envelope is an envelope glycoprotein.

In additional embodiments of the method the DC-SIGN blocker comprises a binding moiety of the viral effector molecule. In some embodiments of the invention in which the viral effector molecule is a molecular constituent of the viral envelope the DC-SIGN blocker that is used comprises a binding moiety of the envelope glycoprotein.

In a preferred embodiment, the viral infection is a CMV infection and the viral effector molecule is a CMV effector molecule. In a further preferred aspect the mammal is a human. In some embodiments the CMV effector molecule is a molecular constituent of the CMV envelope. In further embodiments the molecular constituent of the CMV envelope is a CMV envelope glycoprotein. In yet further embodiments the CMV envelope glycoprotein is CMV envelope glycoprotein B.

Included among embodiments of the invention in which the viral infection is a CMV infection and the viral effector molecule is a CMV effector molecule are embodiments where the DC-SIGN blocker comprises a binding moiety of the CMV effector molecule; the DC-SIGN blocker comprises a binding moiety of the CMV envelope glycoprotein B; the DC-SIGN blocker is a recombinantly produced protein; and the DC-SIGN blocker is an antibody. Among embodiments where the DC-SIGN blocker is an antibody are embodiments where the antibody is a monoclonal antibody; the mammal is a human and the monoclonal antibody is humanized; the antibody specifically binds DC-SIGN; the monoclonal antibody is Mab 1B10.2.6; and the antibody specifically binds the CMV effector molecule. Among embodiments where the antibody specifically binds the CMV effector molecule are embodiments where the CMV effector molecule is CMV envelope glycoprotein B.

In one preferred embodiment of the invention the effector molecule and the DC-SIGN blocker are the same. In a second preferred embodiment the effector molecule and the DC-SIGN blocker are different.

It is interesting that CMV, Ebola, and HIV (as well as SIV) can bind to DC-SIGN. HIV binding to dendritic cells is mediated by the binding of the gp120 glycoprotein of HIV with DC-SIGN. Thus, gp120 is a viral effector molecule. The invention thus provides a method for the prevention and treatment of an Ebola invention and an HIV infection. Specifically, it is an object of the invention to provide a method of preventing or treating an Ebola, HIV or SIV infection of a human or a simian. The method comprises administering to the human or simian an amount of a DC-SIGN blocker that is sufficient to inhibit the interaction of Ebola, HIV or SIV with DC-SIGN receptor present on dendritic cells of the human or simian to thereby prevent or treat the Ebola, HIV or SIV infection.

DC-SIGN is also believed to have a critical role in mediating the known loose adhesion that takes place between dendritic cells and T cells in the apparent absence of foreign antigen. This adhesion is thought to be necessary to provide an opportunity for the TCR to scan the dendritic cell surface and identify the very small amounts of TCR ligand which are present, and in turn to become activated by this ligand. For this reason, the interaction between DC-SIGN on dendritic cells, and ICAM-3 on T cells, is likely to be critically important for the process of T cell activation and stimulation. This model suggests that the DC-SIGN-ICAM-3 interaction may have a role in mediating and/or potentiating other stimulatory effects of dendritic cells on T cells.

For this reason DC-SIGN blockers may be potent anti-inflammatory agents, by blocking the interaction of the ICAM-3 effector molecule with DC-SIGN. Accordingly, the invention also provides a method of preventing or treating inflammation in a mammal caused by interaction of ICAM-3 present on T cells of the mammal with DC-SIGN receptor present on dendritic cells of the mammal. The method comprises administering to the mammal an amount of a DC-SIGN blocker that is sufficient to inhibit the interaction of ICAM-3 present on T cells of the mammal with DC-SIGN receptor present on dendritic cells of the mammal to thereby prevent or treat inflammation.

The invention also provides pharmaceutical compositions comprising a DC-SIGN blocker. Such compositions may be suitable for pharmaceutical use and administration to patients. The compositions typically contain a purified DC-SIGN blocker at a therapeutically achievable concentration and a pharmaceutically acceptable excipient. As used herein, the phrase "pharmaceutically acceptable excipient" includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions can also contain other active compounds providing supplemental, additional, or enhanced therapeutic functions. The pharmaceutical compositions can also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intramuscular, subcutaneous, or via inhalation.

Solutions or suspensions used for subcutaneous application typically include one or more of the following components: a sterile diluent, such as water for injection, saline solution, fixed oils, polyethylene glycols, glycerin, propylene glycol or other synthetic solvents; antibacterial agents, such as benzyl alcohol or methyl parabens; antioxidants, such as ascorbic acid or sodium bisulfite; chelating agents, such as ethylenediaminetetra acetic acid; buffers, such as acetates, citrates or phosphates; and agents for the adjustment of tonicity, such as sodium chloride or dextrose. The pH can be adjusted with acids or bases, such as hydrochloric acid or sodium hydroxide. Such preparations can be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, one may include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the DC-SIGN blocker containing compositions are delivered in the form of an aerosol spray from pressured container or dispenser, which contains a suitable propellant, e.g., a gas such as carbon dioxide, or a nebulizer.

In one embodiment, a purified DC-SIGN blocker is prepared with carriers that will protect it against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions containing LAM can also be used as pharmaceutically acceptable carriers. These can be prepared according to methods known to those skilled in the art, for example, as described in U.S. Pat. No. 4,522,811.

Therapeutically useful agents, such as growth factors (e.g., BMPs, TGF-$\beta$, FGF, IGF), cytokines (e.g., interleukins and CDFs), antibiotics, and any other therapeutic agent beneficial for the condition being treated can optionally be included in or administered simultaneously or sequentially with the DC-SIGN blocker.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of compositions comprising a DC-SIGN blocker can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. DC-SIGN blockers which exhibit large therapeutic indices are preferred.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any DC-SIGN blocker used in the present invention, the therapeutically effective dose can be estimated initially from cell culture assays. A dose can be formulated in animal models to achieve a circulating plasma concentration range that includes the IC50 (i.e., the concentration of the test DC-SIGN blocker which achieves a half-maximal inhibition of symptoms) as determined in cell culture. Levels in plasma can be measured, for example, by high performance liquid chromatography. The effects of any particular dosage can be monitored by a suitable bioassay.

A targeting complex of the present invention comprises at least one DC-SIGN blocker molecule covalently attached to at least one subject molecule. In some embodiments, a single DC-SIGN blocker molecule is covalently linked to a single subject molecule. In other embodiments, more than one DC-SIGN blocker molecule can be covalently linked to a single subject molecule. The multiple DC-SIGN blocker molecules can each be independently covalently linked to the subject molecule; alternatively, one or more of the more than one DC-SIGN blocker molecules can be covalently linked only to one or more other DC-SIGN blocker molecules, at least one of which is itself covalently linked to the subject molecule.

In other embodiments, multiple subject molecules are covalently linked to a single DC-SIGN blocker molecule. The multiple subject molecules can each be independently covalently linked to the DC-SIGN blocker molecule; alternatively, one or more of the more than one subject molecules can be covalently linked only to one or more other subject molecules, at least one of which is itself covalently linked to the DC-SIGN blocker molecule.

Additional embodiments of the invention utilize compositions of more than one of the various types of DC-SIGN blockers described immediately above. There is no limit to the diversity of such compositions which can be used. One of skill in the art will appreciate that the composition to be used for a particular application will be dictated by many factors and that a suitable composition can thus be appropriately chosen for each application of the invention.

Techniques for making the DC-SIGN blockers of the invention are well known and widely practiced by those of skill in the biochemistry art, and thus need not be detailed here. However, one of skill in the art will recognize that any suitable technique which results in the formation of a covalent bond between a subject molecule and a DC-SIGN blocker molecule can be used.

Subject molecules can be any molecule of interest. Non-limiting examples include: small organic molecules, proteins, nucleic acids, carbohydrates, and lipids. One of ordinary skill in the art will appreciate that any known derivatives and composites of one or more of these classes of molecules can also be used.

In the case in which the subject molecule is a protein, nucleic acid, carbohydrate, or lipid, the subject molecule can be obtained from a natural source, i.e., purified from an organism, which comprises the molecule. Alternatively, the subject molecule can be obtained from a recombinant source, i.e., from a recombinant organism, which has been engineered to produce a subject molecule of choice. In some cases, the recombinant organism that is used to produce the subject molecule is one that comprises the subject molecule, as the organism occurs in nature, in nonrecombinant form. In other cases, the subject molecule is one that does not naturally occur in the recombinant organism.

The subject molecules of the invention also include derivatives of small organic molecules, proteins, nucleic acids, carbohydrates, and lipids. As used here, a derivative is a form of small organic molecule, protein, nucleic acid, carbohydrate, or lipid that is modified from its natural state by adding, subtracting, or altering one or more chemically reactive sites present on the small organic molecule, protein, nucleic acid, carbohydrate, or lipid. Techniques for making derivatives of small organic molecules, proteins, nucleic acids, carbohydrates, and lipids are well known and widely practiced by those of skill in the biochemistry art, and thus need not be detailed here.

In a preferred embodiment the subject molecule is an antibody.

The subject molecule can also be a molecule that is antigenic. A molecule is antigenic when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The targeting complex of the invention can be exposed to a dendritic cell either in vivo or in vitro. In vivo exposure is achieved by administering the targeting complex in a pharmaceutical composition as described herein or in any suitable equivalent formulation known in the art. In that case, the targeting complex will bind to DC-SIGN on the surface of dendritic cells in vivo. In vitro exposure occurs when dendritic cells grown in vitro are exposed to the targeting complex.

The following examples aid in describing certain aspects of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention.

EXAMPLES

Example 1

Herpesviruses

AD169, Towne (CMV laboratory strains) and TB40/E (CMV clinical isolate) were provided by Dr. S. Michelson (Institut Pasteur, Paris, France) and Dr. C. Sinzger (Tubingen, Germany), respectively. ADGFP is a genetically modified AD169 strain encoding an Enhanced Green Fluorescent Protein driven by the CMV immediate-early gene promoter (Borst et al., 2001). VZV and HSV-1 clinical isolates were obtained from Dr. Isabelle Garrigue (Laboratory of Virology, CHU Pellegrin, Bordeaux, France).

Example 2

Reagents, Antibodies and Viral Glycoproteins

Mannan and EGTA were purchased from Sigma-Aldrich Corporation (Saint Louis, Mo.). Soluble viral envelope glycoproteins were produced and purified from mammalian or insect cells. HIV-1 gp120 (MN isolate) was obtained from the NIBSC repository (Medical Research Council, United Kingdom). VZV gB and VZV gE (Jacquet et al., 1995) were gifts from Dr. A. Jacquet, (Department of Applied Genetics, Gosselies, Belgium). HSV-1 gB and HSV-1 gD (Sisk et al., 1994) were provided by Dr. G. H. Cohen (University of Pennsylvania, Philadelphia, Pa.). Expression and purification of CMV gB (gift of Dr Claude Meric, Aventis Pasteur, Marcy L'Etoile, France) were previously described (Norais et al., 1996; Pass et al., 1999). Anti-CMV gB (clone 1-M-12, IgG1) and anti-DC-SIGNR (clone 120604, IgG2a) mAbs were purchased from Biodesign International (Saco, Me.) and R&D Systems (Minneapolis, Minn.), respectively. Anti-LIF 7D2 (Taupin et al., 1993) and anti-SDF-1 K15C monoclonal antibodies (mAb) (Amara et al., 1999) were used as isotypic controls.

Example 3

Cells

MRC-5 (Bio Mérieux S.A., Marcy l'Etoile, France) and U373 MG (ECCC, Salisbury, United Kingdom) are CMV-, HSV-1- and VZV-permissive cell lines, from fibroblastic and astrocytic origine, respectively. Parental and DC-SIGN+ THP-1 cells (wild type and Δ35 and Δ20 mutants lacking the first 35 and 20 amino acids of the cytoplasmic domain, respectively) (Kwon et al., 2002) were a gift from Dr. D. R. Littmann (Skirball Institute of Biomolecular Medicine, New York, N.Y., USA). DC-SIGN+ HeLa cells were generated by infecting HeLa cells with an HIV-derived vector (TRIP-αU3 vector, a gift from Dr. P. Charneau, Institut Pasteur, Paris) encoding a human DC-SIGN cDNA. MD-DC were generated from peripheral blood monocytes treated with 20 ng/mL IL-4 (Schering-Plough, Kenilworth, N.J.) and 100 ng/mL GM-CSF (Leucomax, Novartis-Pharma, Rueil Malmaison, France) (Romani et al., 1994). At day 5, virtually the totality of cells displayed the phenotype CD1a+, HLA-DR+, $CD80^{low}$, $CD86^{low}$, CD83−, CD14− characteristic of immature MD-DC.

Example 4

DC-SIGN cDNA and anti-DC-SIGN Antibodies

DC-SIGN cDNA was isolated from human immature MD-DC by RT-PCR. For expression in mammalian cells, human DC-SIGN was subcloned at the EcoR1/Xba 1 sites of the pcDNA3 myc-His (version A) plasmid (Invitrogen, Carsbad, Calif.). The DC-SIGNR cDNA was a gift from Dr R. W. Doms, (University of Pennsylvania, Philadelphia, Pa.). Anti-DC-SIGN clone 1B10.2.6 (IgG2a) was obtained by immunizing BALB/c mice with HEK 293T cells transfected with DC-SIGN cDNA, screened by indirect immunofluorescent staining and FACS analysis on DC-SIGN+ HeLa cells and used as purified immunoglobulins.

Example 5

Infection Assays

For trans-infection experiments, cells were incubated with viral suspensions (CMV, VZV or HSV-1, MOI=1) for 2 hr, at 37° C. Thereafter, unbound viral particles were removed by extensive washes and cells were co-cultured with sub-confluent MRC-5 or U373 MG cell monolayers. After 24 to 72 hr, infected MRC-5 or U373-MG cells were fixed, permeabilized and stained with specific mAbs directed against IEA- or EA-CMV (mAbs E13 and 2A2, respectively), VZV (mAb 2013) or HSV (mAb CHA-437) (Argen Biosoft, Varilhes, France). When indicated MD-DC or THP-1 (parental or DC-SIGN+) cells were incubated with EGTA (5 mM), mannan or anti-DC-SIGN (1B10.2.6 mAb) for 30 minutes at 4° C. prior challenge with infectious preparations. Infection by ADGFP strain was assessed by counting GFP-expressing cells at day 3. For long term infectivity experiments DC-SIGN+ or parental THP-1 cells were incubated with ADGFP (MOI=1) for 4 hr at 37° C. After extensive washes, infected cells were incubated at 37° C. and an aliquot of these cells was added to a sub-confluent MRC-5 cell culture every 2 days during the assay.

To assess the effect in cis of DC-SIGN during infection, cells were incubated with low titers of CMV (MOI=0.1) for 2 hr at 37° C. Non internalized viral particles were removed by washes in low pH citrate buffer (pH=3). The number of infected cells was determined by immunocytochemistry 72 hours after infection. Supernatants from infected cells kept in culture for 14 days were harvested to quantify de novo generated virions by plaque-assay titration.

Example 6

HIV-1 gp120 Binding Competition and CMVgB Direct Binding Assays

DC-SIGN+ THP-1 cells were washed two times, resuspended in ice-cold binding buffer (1 mM $CaCl_2$, 2 mM $MgCl_2$ and 0.1% Bovine Serum Albumin in PBS) at $10^6$ cells/mL and pre-treated or not for 15 minutes with competitors (20 μg/ml). Thereafter, recombinant biotinylated CXCR4-tropic (MN isolate) HIV-1 gp120 (2 μg/ml; Immunodiagnostics Inc., Woburg, Mass.) was added for 30 minutes at 4° C. After extensive washing, cell-bound biotinylated HIV-1 gp120 was revealed by flow cytometry using FITC-conjugated Streptavidin (Immunotech SA, Marseille, France). For CMV gB binding experiments, recombinant soluble CMV gB and Bovine Serum Albumine (BSA; Amersham Pharmacia Biotech, Uppsala, Sweden) were biotinylated with sulfo-NHS biotin, according to manufacturer instructions (Pierce, Rockford, Ill.).

Example 7

Analysis of DC-SIGN Interactions with Viral Envelope Glycoproteins by SPR

The cDNA coding for the DC-SIGN CRD (amino acids 254-404) was obtained by PCR and cloned into pET15b (Novagen). The protein was expressed in *Escherichia coli* C41 (DE3) as inclusion bodies. Refolding of the protein has been done by dilution and dialysis as described (Mitchell et al., 2001). Purification of refolded DC-SIGN CRD has been achieved in two steps: first on a Ni-NTA (QIAGEN) column equilibrated in 25 mM Tris Cl pH 7.8, 150 mM NaCl, 4 mM $CaCl_2$ (Loading Buffer) and eluted with a linear gradient of imidazole and second on a Mannose-agarose column equilibrated in Loading Buffer, and eluted in buffer where $CaCl_2$ was replaced by EDTA (10 mM). Pooled fractions are then concentrated and dialyzed against Loading Buffer.

Four flow cells of a Biacore B1 sensor chip were activated as described (Amara et al., 1999). The first flow cell was then blocked with 50 µl of 1 M.ethanolamine pH 8.5 and served as a control surface. The three other ones were treated with soluble gp120, gB CMV or gB HSV (concentration range 1-10 µg/ml in 10 mM acetate buffer pH 5). Typically, this procedure permitted the coupling of approximately 250-350 resonance units (RU) of proteins. For binding assays, DC-SIGN CRD was diluted in Loading Buffer and was allowed to react with the sensor chip (at 30 µl/min). In a typical analysis, DC-SIGN CRD (0.13 to 1 µM, see figure legend) was injected over the four flow cells for 8 min, after which the complexes were rinsed with buffer to analyze the dissociation phase. The surface was then regenerated with a 6 min pulse of running buffer containing 50 mM EDTA instead of $CaCl_2$. Sets of sensorgrams were analyzed using the BIAevaluation 3 software.

Example 8

Expression of DC-SIGN at the Cell Membrane Enables Binding of CMV

The capacity of CMV to bind DC-SIGN was investigated. Parental and DC-SIGN$^+$ THP-1 cells, or immature monocyte-derived DC (MD-DC) were incubated on ice with increasing concentrations of CMV and the presence of cell-bound virions was quantified by flow cytometry using a mAb directed against the CMV gB. While parental THP-1 cells failed to bind detectable amounts of CMV, both DC-SIGN-expressing THP-1 and MD-DC absorbed CMV virions in a dose dependent manner (FIG. 1B). Prevention of CMV gB antibody-labeling by acidic washes proved the existence of cell-bound virions (FIG. 1B). Abrogation of virion attachment observed following pre-incubation of cells with mannan, a complex sugar that binds to the Carbohydrate Recognition Domain (CRD) of lectins, suggests that the CMV-DC-SIGN interaction is accounted by the glycosylated residues of CMV envelope glycoproteins.

Example 9

Transmission of CMV Infection to Permissive Cells is Mediated by DC-SIGN

Figure 2:
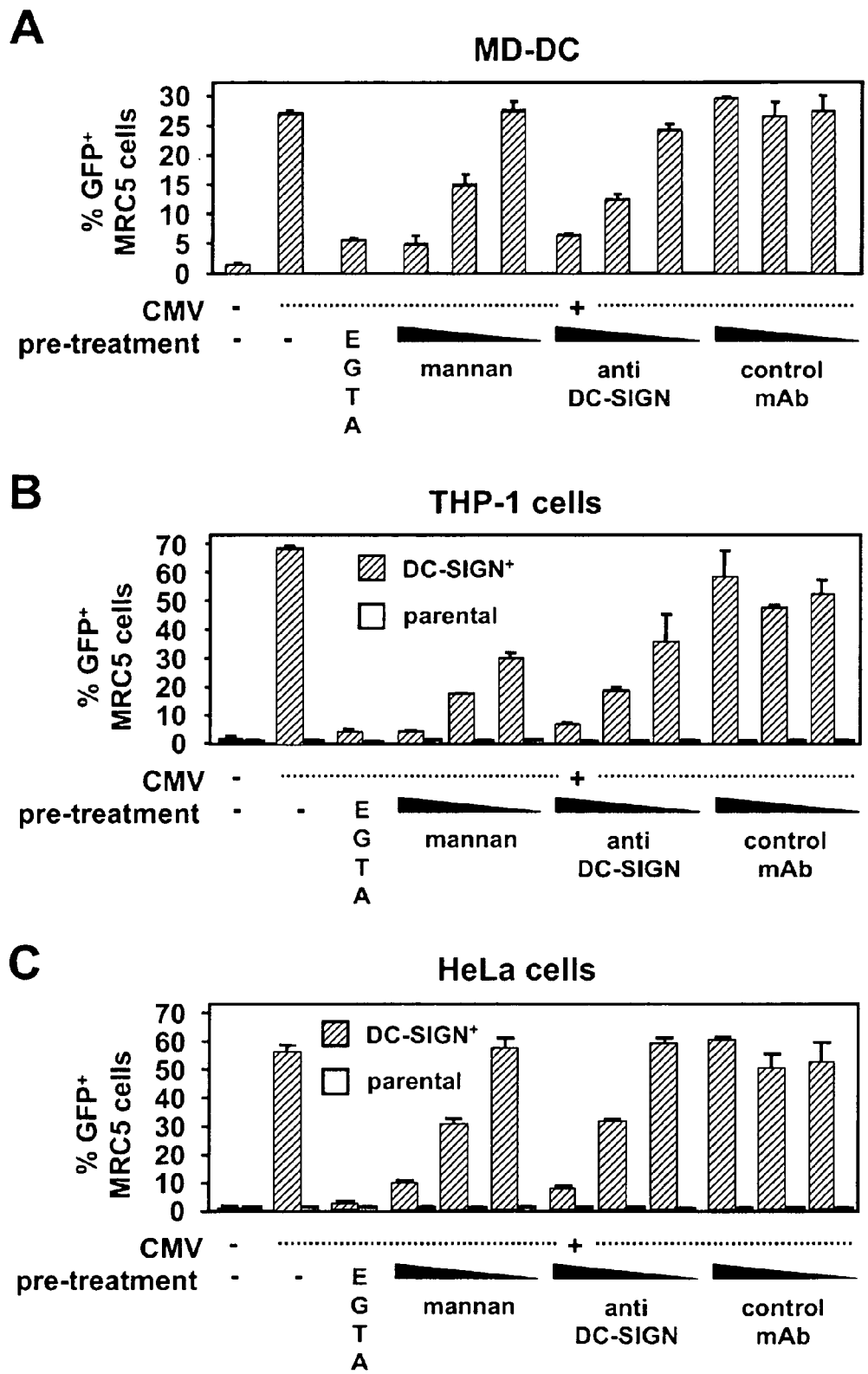

MD-DC, THP-1 or HeLa expressing DC-SIGN were incubated with a mutant CMV strain encoding a GFP (ADGFP) (Borst et al., 2001). HeLa cells were selected for their refractoriness to CMV infection (Einhorn et al., 1982; Tsutsui et al., 1987) which persists despite transduction with DC-SIGN (our unpublished observations). MD-DC (FIG. 2A), DC-SIGN$^+$ THP-1 (FIG. 2B) and DC-SIGN$^+$ HeLa cells (FIG. 2C), in contrast to parental THP-1 or HeLa cells, conveyed CMV infection as proved by the expression of GFP in MRC-5 cells. Trans-infection of MRC-5 cells was prevented by pre-incubating MD-DC, DC-SIGN$^+$ THP-1 or DC-SIGN$^+$ HeLa cells either with EGTA or mannan before being pulsed with CMV. Moreover, the anti-DC-.SIGN mAb 1B10.2.6, which blocks HIV transmission (data not shown), also inhibited efficiently the transmission of CMV from DC-SIGN$^+$ cells to MRC-5 cells. We conclude that trans-infection of CMV to susceptible cells is accounted for by DC-SIGN and does not require productive infection by DC-SIGN-expressing cells.

Figure 3:
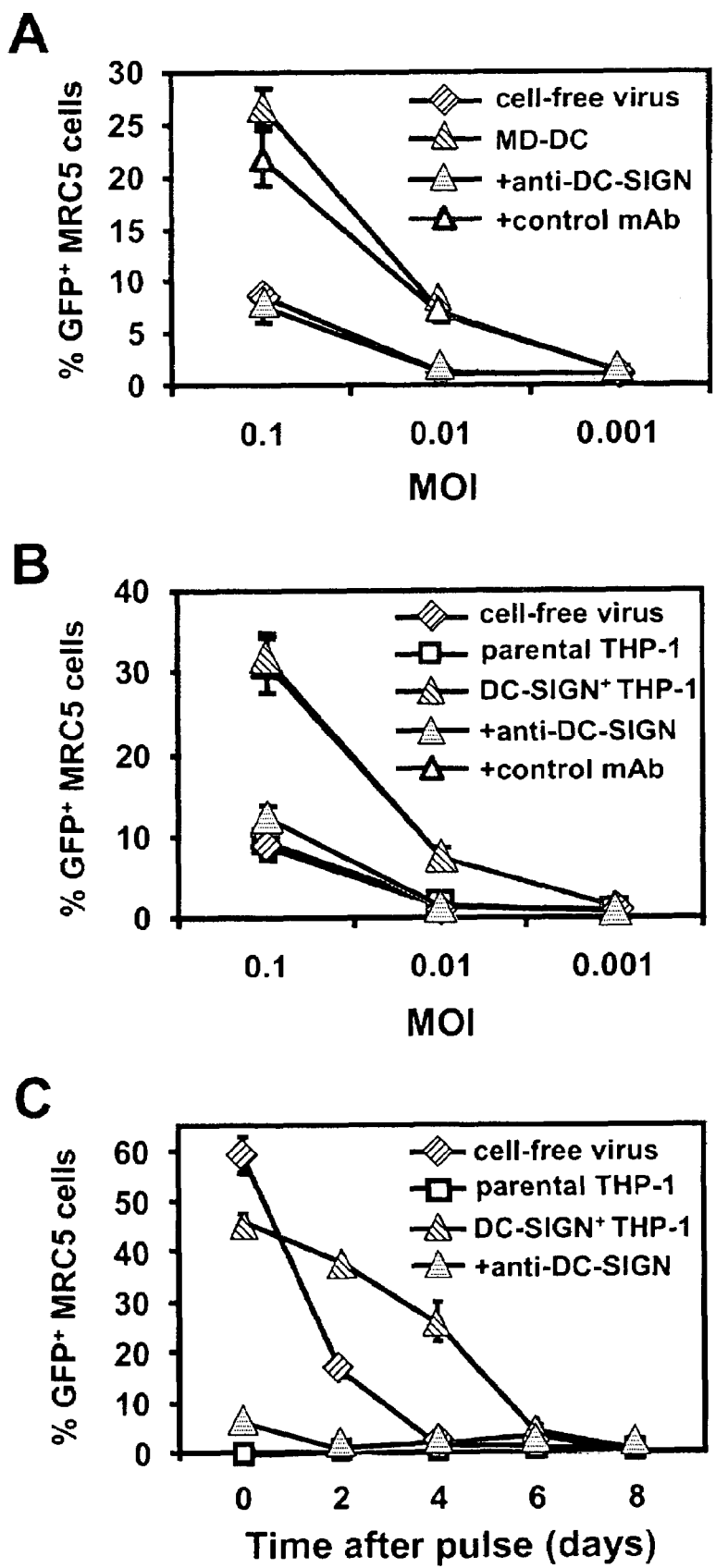

The capacity of DC-SIGN to enhance infectiveness of CMV was assessed. To these purposes, MRC-5 cells were either incubated with low titers of cell-free CMV or co-cultured with MD-DC (FIG. 3A) or DC-SIGN$^+$ THP-1 (FIG. 3B) previously pulsed with identical amount of CMV. Co-culture of MRC-5 with CMV-pulsed DC-SIGN$^+$ cells lead to a substantial enhancement of MRC-5 infections as compared to MRC-5 exposed to cell-free virus. The enhancement of CMV infectivity conferred by DC-SIGN$^+$ cells pulsed with CMV was abrogated by specific anti-DC-SIGN mAb 1B10.2.6 (FIGS. 3A and 3B). To determine if DC-SIGN-bound CMV retains infectivity over a more prolonged period of time than free virus, DC-SIGN$^+$ THP-1 were pulsed with CMV, washed and cultured at 37° C. for different periods before co-culture with MRC-5 cells. In parallel, cell-free virus was incubated for the same period of time at 37° C. before being added to MRC-5 cells. Our findings show that CMV remains infectious for 4-5 days when bound to DC-SIGN whereas cell-free virus retains its infectivity only for 2 days (FIG. 3C).

Figure 4:
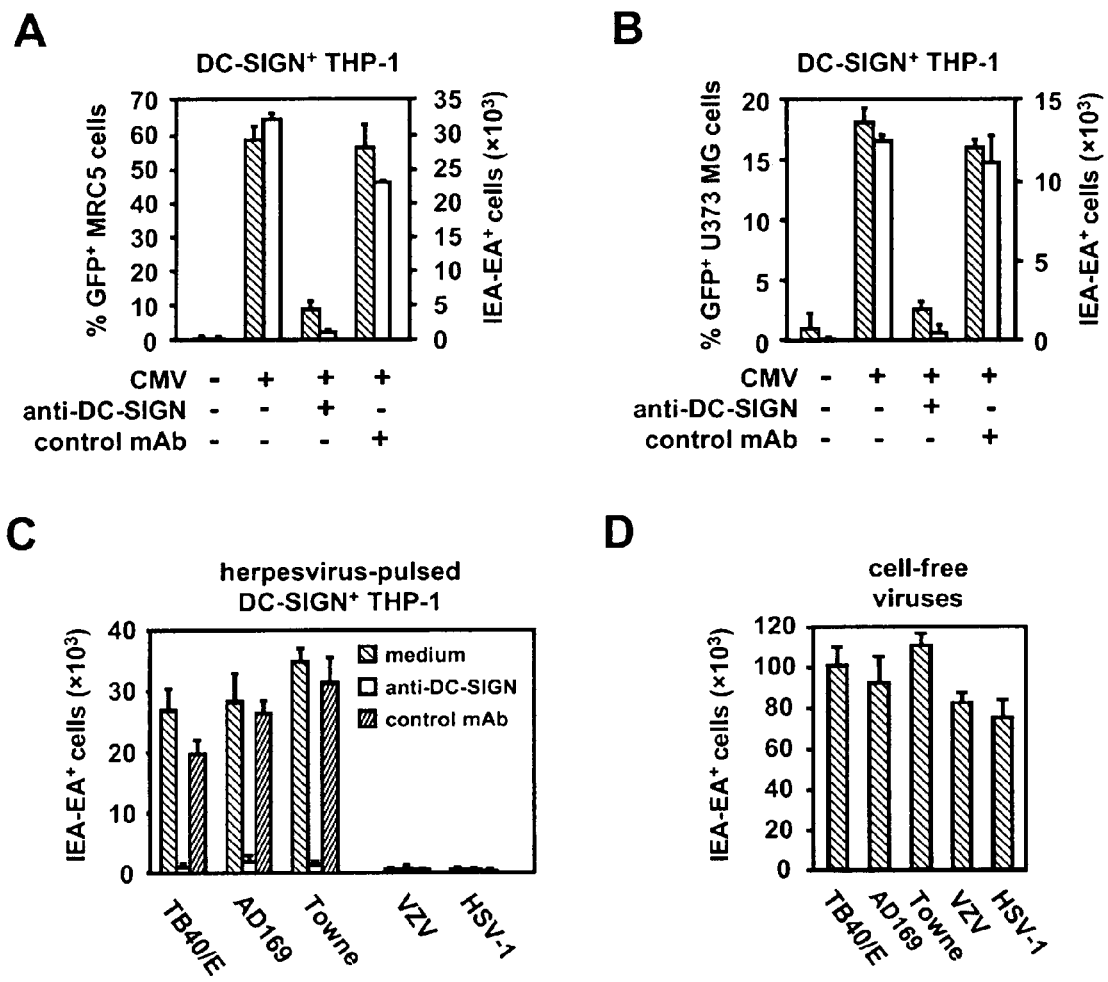

In parallel, the detection by immunostaining of early markers of CMV replication (intranuclear immediate early and early antigens, IEA and EA, respectively) has been done (FIG. 4A). The findings obtained by this alternative assay confirmed the role of DC-SIGN in the transmission of CMV to permissive cells and validated the trans-infection assay. Transmission of CMV from DC-SIGN$^+$ cells is not restricted to a particular permissive cell type since DC-SIGN$^+$ THP-1 cells also transmitted infectious virions to the U373 MG astrocytoma cell line (FIG. 4B).

We next aimed at determining if other members of the herpesviridae family have the same capacity as CMV to interact with DC-SIGN. To this purpose, DC-SIGN$^+$ THP-1 cells were exposed to clinical isolate of CMV, HSV-1 or VZV and thereafter co-cultured with MRC-5 cells which are fully susceptible to the three viruses (FIG. 4D). Expression of CMV-, but not HSV-1- or VZV-EA or -IEA in MRC-5 cells is compatible with a high degree of specificity for the interaction of DC-SIGN with CMV envelope glycoproteins (FIG. 4C).

Example 10

DC-SIGN Cytoplasmic Tail is Critical for Enhanced Transmission of CMV

Figure 5:
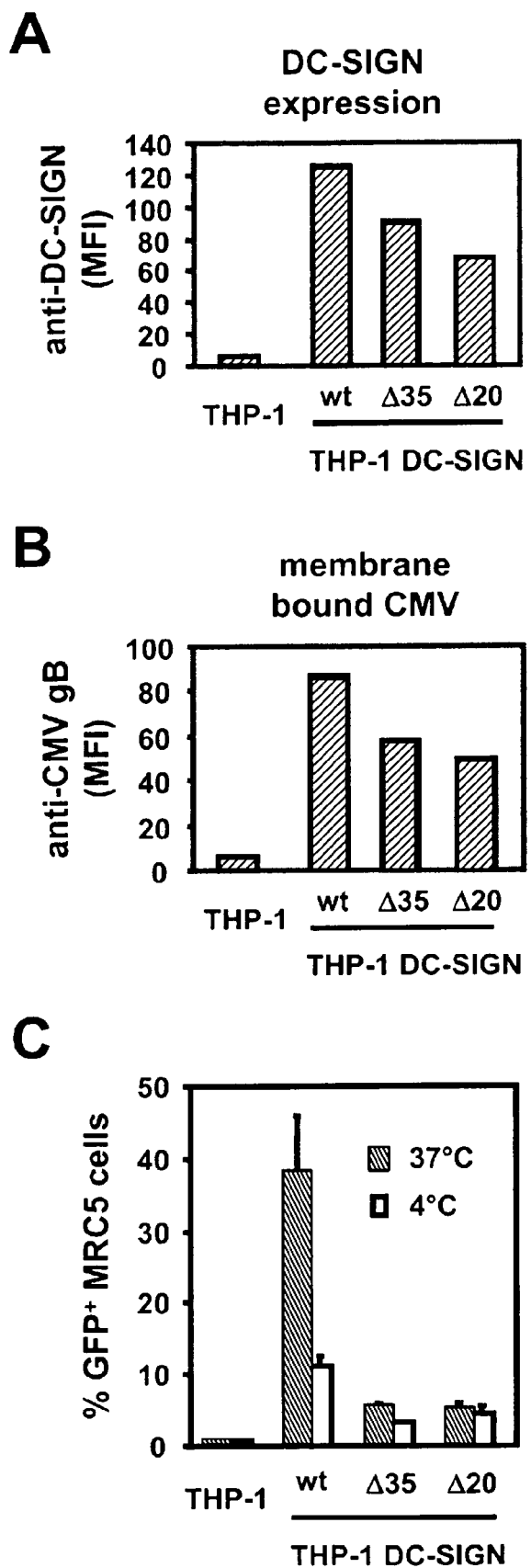

The role proposed for DC-SIGN internalisation for trans-enhancement of HIV infection was assessed for CMV transmission from DC-SIGN$^+$ cells to susceptible cells. To this purpose, THP-1 cells expressing mutant forms of DC-SIGN (Kwon et al., 2002) encoding either combined deletion of dileucine and tyrosine-based motifs (DC-SIGN A35), or the dileucine-based motif only (DC-SIGN Δ20), which are putative internalization motifs required for DC-SIGN endocytosis, were exposed to low MOI CMV infection. Both DC-SIGN mutants were expressed in THP-1 cells with similar efficiency as the wild type counterpart (FIG. 5A). Moreover, they displayed roughly comparable capacities to bind CMV particles (FIG. 5B). Parental and DC-SIGN-expressing (either wt or mutated) THP-1 cells were then assessed for their ability to transmit CMV to permissive MRC-5 cells. We found that following incubation with ADGFP CMV at 37° C., DC-SIGN Δ35- or DC-SIGN Δ20-expressing THP-1 cells showed a marked decreased capacity to transmit CMV as compared to DC-SIGN+ THP-1 cells (FIG. 5C). Incubation on ice of DC-SIGN wt-expressing THP-1 cells with CMV prevented virus transmission to MRC-5 cells (FIG. 5C). These results suggest that, similarly to HIV infection, trans-enhancement of CMV infection by DC-SIGN-expressing cells requires the cytoplasmic domain of DC-SIGN.

Example 11

Figure 6:
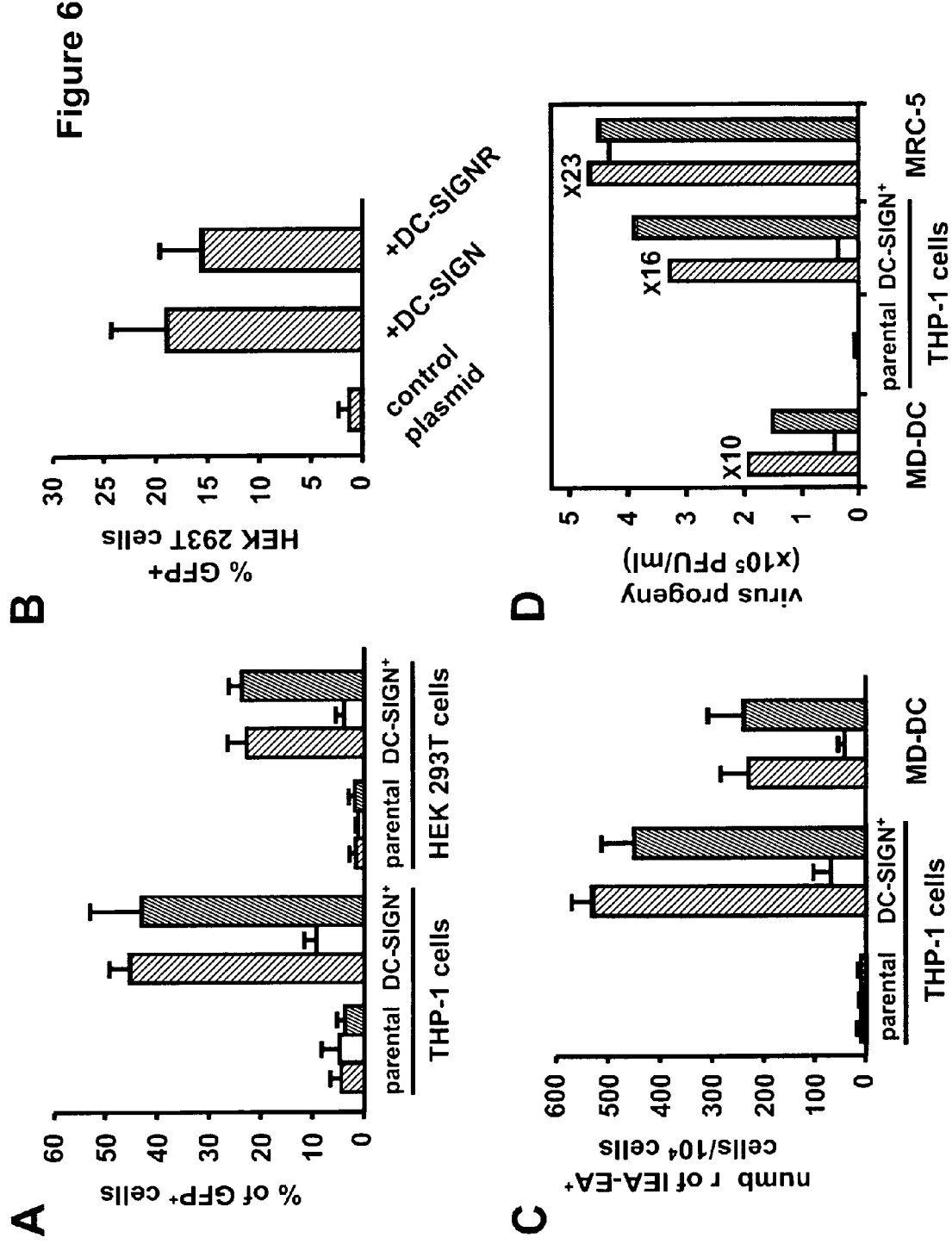

DC-SIGN Expression Renders Low-Susceptible Cells Sensitive to CMV Infection and Mediates the Infection of MD-DC by Primary CMV Isolates We next investigated whether DC-SIGN is involved in cis in the entry of CMV into host cells. Two complementary approaches were developed to this purpose. First, using either HEK 293T or THP-1 cells transduced with DC-SIGN, we evaluated their capacity to support CMV infection. It has been previously reported that undifferentiated THP-1 are unable to support CMV IE gene expression despite virus entry (Lashmit et al., 1998; Weinshenker et al., 1988). We confirmed this finding and show that HEK 293T cell line similarly appears to be poorly susceptible to CMV infection (ADGFP virus). In sharp contrast with these findings, both HEK 293T and THP-1 expressing DC-SIGN were highly susceptible to CMV infection. Indeed, more than 14% of DC-SIGN+ THP-1 cells were positive for GFP after 2 hours of contact with CMV ADGFP followed by a 2 days incubation while no GFP expression was found in parental cells (FIG. 6A). Similarly to DC-SIGN, the homologous DC-SIGNR lectin was capable to render HEK 293T susceptible to CMV infection (FIG. 6B). Conclusive evidence about the role played by DC-SIGN in the infectiveness of transduced cells came from the drastic reduction of the CMV IE gene expression levels in both DC-SIGN+ THP-1 and HEK 293T cells in the presence of anti-DC-SIGN mAb (FIG. 6A).

MD-DC, which show natural expression of DC-SIGN, were used to confirm and extend the findings observed in the first set of experiments. By opposition to THP-1 cells, MD-DC are known to be permissive to infection by primary CMV isolates. Detection of IEA and EA in a substantial number of MD-DC when incubated with TB40/E proved the susceptibility of these cells to non-adapted, clinical CMV strains. Amazingly, pre-incubation of MD-DC with the anti-DC-SIGN 1B10.2.6 mAb prevented their infection by CMV with roughly the same efficiency as it did in DC-SIGN+ THP-1 cells (FIG. 6C).

Full replication of CMV in DC-SIGN-expressing cells was then assessed by quantifying the progeny of infectious virions. MRC-5, MD-DC, DC-SIGN+ or parental THP-1 cells were incubated with low titers of a primary CMV strain, washed in acidic buffer to remove non internalized virus and thereafter cultured for 14 days. The generation of infectious CMV virions from these cells was quantified by plaque assay titration on MRC-5 cells. Accumulation of CMV virions was detected in culture supernatants from MD-DC and DC-SIGN+ THP-1 cells (FIG. 6D). The amount of infectious virions released by MD-DC or DC-SIGN-expressing THP-1 were 10 and 16 times, respectively, more elevated than the number of input virus used at day 0 and were comparable to amounts released by MRC-5 cells (FIG. 6D). Pre-incubation of MD-DC or DC-SIGN+ THP-1 with the specific anti-DC-SIGN 1B10.2.6 mAb precluded detectable generation of CMV infectious virions thus demonstrating the involvement of DC-SIGN in the cis-infection of DC-SIGN-expressing cells (FIG. 6D).

Hence, these results imply that in cis cell surface expression of DC-SIGN not only potentiates the expression of CMV IE gene products but also confers to CMV low susceptible cells the capacity to support a full replicative cycle in the host cell. These findings suggest a crucial biological role of DC-SIGN in the propagation of the CMV natural infection by DC.

Identification of CMV glycoprotein B as a viral ligand of DC-SIGN Since DC-SIGN was shown to bind HIV particles through a specific interaction between the Carbohydrate Recognition Domain (CRD) of DC-SIGN and sugar moities of HIV-1 gp120 (Mitchell et al., 2001), we searched for an equivalent of HIV-1 gp120 on CMV particles. The human CMV virion is known to harbor several different envelope glycoproteins. Among them, CMV gB, gH and gM were shown to be directly involved in two early events of the CMV infection: CMV attachment and fusion between viral and cellular membranes (Compton et al., 1993; Kari and Gehrz, 1992; Milne et al., 1998). The reasons for focusing our research on CMV gB are manifold. First, CMV gB is the most abundant and the most extensively N- and O-glycosylated envelope glycoprotein of CMV (Gibson, 1983). Second, it has been demonstrated that sequence variations in CMV gB from different strains of human CMV are lower than in other CMV envelope glycoproteins (Chou and Dennison, 1991). Third, CMV gB has been proposed to play central roles in virion penetration into cells, transmission from cell to cell, and fusion of infected cells (Navarro et al., 1993).

Figure 7:
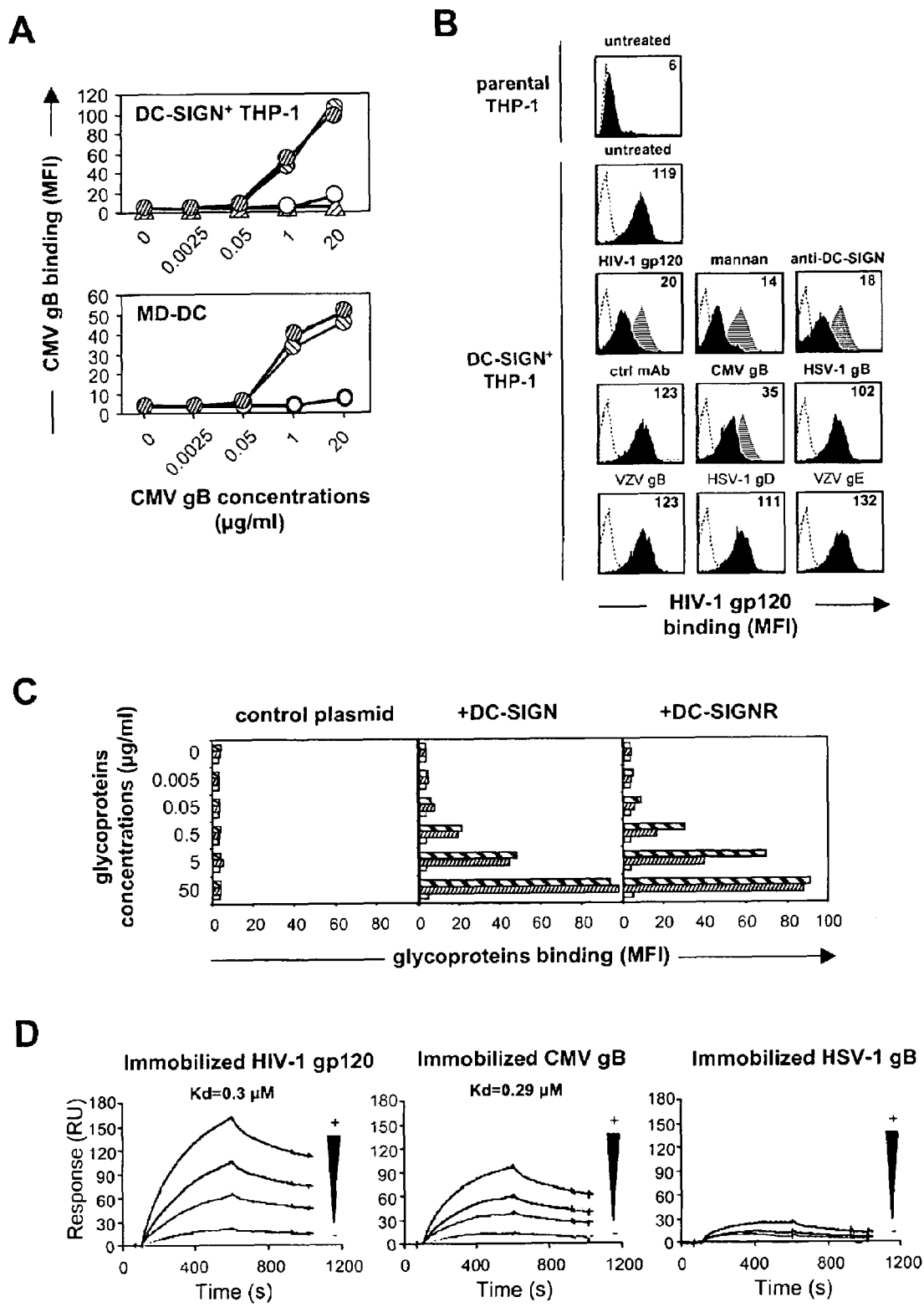

Recombinant, biotinylated CMV gB was directly bound and detected on DC-SIGN-expressing THP-1 cells or MD-DC, but not on parental THP-1 (FIG. 7A) and similar findings were observed with unlabelled CMV gB (data not shown). The attachment of CMV gB to cells was specifically abrogated by pre-incubation with the blocking anti-DC-SIGN 1B10.2.6 mAb. Futher authentification of CMV gB as a CMV DC-SIGN ligand came from a competition assay with other viral envelope glycoproteins. In this assay we pre-incubated DC-SIGN+ THP-1 cells with purified HIV-1 gp120, CMV gB, HSV-1 gB, VZV gB, HSV-1 gD or VZV gE. Following exposure to each single envelope glycoprotein, cells were incubated with biotinylated HIV-1 gp120, which binding to DC-SIGN+ THP-1 cells was evidenced by immunostaining and FACS analysis. Among the herpesvirus proteins assessed, only CMV gB decreased the binding of biotinylated HIV-1 gp120 on DC-SIGN. This competitive effect of CMV gB was almost as efficient as that shown by unlabelled HIV-1 gp120, mannan or anti-DC-SIGN mAb 1B10.2.6 (FIG. 7B). Pre-treatment of DC-SIGN+ THP-1 cells and MD-DC with recombinant CMV gB before incubation with CMV virions also efficiently blocked transmission of CMV to susceptible MRC-5 cells (data not shown).

To investigate whether DC-SIGNR could also bind to CMV gB, we incubated HEK 293T cells transiently transfected with cDNA encoding DC-SIGN or DC-SIGNR in the presence of biotinylated-HIV-1 gp120, -CMV gB or -BSA (FIG. 7C). No binding was observed when incubating transfected cells with the control BSA. In contrast, both HIV-1 gp120 and CMV gB efficiently bound to HEK 293T cells expressing either DC-SIGN or DC-SIGNR. Both interactions were calcium-dependent since they were blocked by EGTA (data not shown). Surprisingly, at low concentrations CMV gB displayed a higher apparent affinity than HIV-1 gp 120 for DC-SIGNR, whereas both viral glycoproteins bound to DC-SIGN-expressing cells with comparable efficiency. Together, these results demonstrated that CMV gB is a CMV ligand for DC-SIGN and DC-SIGNR. It deserves to be investigated whether this capacity is restricted to CMV gB or is shared by other CMV envelope glycoproteins.

Example 12

Characterization of DC-SIGN-Glycoproteins Interactions

The surface plasmon resonance (SPR) technology was used to further analyze the characteristics of DC-SIGN binding to HIV-1 gp120 and CMV gB in vitro. Typical sensorgrams were obtained by injection of a concentration range of recombinant soluble CRD domain of DC-SIGN (0.13 to 1 µM) over surfaces functionalized with HIV-1 gp120 (FIG. 7D, left panel), CMV gB (FIG. 7D, middle panel) or HSV-1 gB (FIG. 7D, right panel). Visual inspection of the binding curves immediately showed that DC-SIGN binds to HIV-1 gp120 and CMV gB, while only displaying negligible binding to HSV-1 gB. Binding of DC-SIGN CRD to both HIV-1 gp120 and CMV gB was strongly inhibited by the anti-DC-SIGN 1B10.2.6 mAb and EDTA (data not shown). The binding curves were then individually fitted to a Langmuir model (A+B=AB). This analysis returned an average on rate $k^{on}=3.33\times10^3$ $M^{-1}S^{-1}$, and off rate $k_{off}=1.01\times10^{-3}S^{-1}$, thus giving a equilibrium dissociation constant of 0.30 µM for HIV-1 gp120, and $k_{on}=4.4\times10^3 M^{-1}S^{-1}$, $k_{off}=1.26\times10^{-3}S^{-1}$, leading to an equilibrium dissociation constant of 0.29 µM for CMV gB. Since the affinity that characterize the DC-SIGN CRD binding to HIV-1 gp120 and to CMV gB are similar, the higher binding level observed with the HIV-1 gp120 activated surface compared to the CMV gB surface (FIG. 7D, left and middle panels) may simply reflect a difference in immobilization or in glycan density between both proteins.

DEPOSITS

The Hela cell line denoted "Hela DC-SIGN Flap" was deposited at the C.N.C.M. on Oct. 30, 2002, under the accession number I-2949.

The DC-SIGN clone denoted "DC-SIGN human clone2" was deposited at the C.N.C.M. on Oct. 30, 2002, under the accession number I-2950.

The hybridoma denoted "1B10.2.6" was deposited at the C.N.C.M. on Nov. 7, 2002, under the accession number I-2951.

REFERENCES

Alvarez, C. P., Lasala, F., Carrillo, J., Muniz, O., Corbi, A. L., and Delgado, R. (2002). C-Type Lectins DC-SIGN and L-SIGN Mediate Cellular Entry by Ebola Virus in cis and in trans. *J Virol* 76, 6841-6844.

Amara, A., Lorthioir, O., Valenzuela, A., Magerus, A., Thelen, M., Montes, M., Virelizier, J. L., Delepierre, M., Baleux, F., Lortat-Jacob, H., and Arenzana-Seisdedos, F. (1999). Stromal cell-derived factor-1alpha associates with heparan sulfates through the first beta-strand of the chemokine. *J Biol Chem* 274, 23916-23925.

Andrews, D. M., Andoniou, C. E., Granucci, F., Ricciardi-Castagnoli, P., and Degli-Esposti, M. A. (2001). Infection of dendritic cells by murine cytomegalovirus induces functional paralysis. *Nat Immunol* 2, 1077-1084.

Baldwin, B. R., Zhang, C. O., and Keay, S. (2000). Cloning and epitope mapping of a functional partial fusion receptor for human cytomegalovirus gH. *J Gen Virol* 81, 27-35.

Banchereau, J., and Steinman, R. M. (1998). Dendritic cells and the control of immunity. *Nature* 392, 245-252.

Bashirova, A. A., Geijtenbeek, T. B., van Duijnhoven, G. C., van Vliet, S. J., Eilering, J. B., Martin, M. P., Wu, L., Martin, T. D., Viebig, N., Knolle, P. A., et al. (2001). A dendritic cell-specific intercellular adhesion molecule 3-grabbing nonintegrin (DC-SIGN)-related protein is highly expressed on human liver sinusoidal endothelial cells and promotes HIV-1 infection. *J Exp Med* 193, 671-678.

Bodaghi, B., Slobbe-van Drunen, M. E., Topilko, A., Perret, E., Vossen, R. C., van Dam-Mieras, M. C., Zipeto, D., Virelizier, J. L., LeHoang, P., Bruggeman, C. A., and Michelson, S. (1999). Entry of human cytomegalovirus into retinal pigment epithelial and endothelial cells by endocytosis. *Invest Ophthalmol Vis Sci* 40, 2598-2607.

Borst, E. M., Mathys, S., Wagner, M., Muranyi, W., and Messerle, M. (2001). Genetic evidence of an essential role for cytomegalovirus small capsid protein in viral growth. *J Virol* 75, 1450-1458.

Boyle, K. A., and Compton, T. (1998). Receptor-binding properties of a soluble form of human cytomegalovirus glycoprotein B. *J Virol* 72, 1826-1833.

Chou, S. W., and Dennison, K. M. (1991). Analysis of interstrain variation in cytomegalovirus glycoprotein B sequences encoding neutralization-related epitopes. *J Infect Dis* 163, 1229-1234.

Compton, T., Nepomuceno, R. R., and Nowlin, D. M. (1992). Human cytomegalovirus penetrates host cells by pH-independent fusion at the cell surface. *Virology* 191, 387-395.

Compton, T., Nowlin, D. M., and Cooper, N. R. (1993). Initiation of human cytomegalovirus infection requires initial interaction with cell surface heparan sulfate. *Virology* 193, 834-841.

Curtis, B. M., Scharnowske, S., and Watson, A. J. (1992). Sequence and expression of a membrane-associated C-type lectin that exhibits CD4-independent binding of human immunodeficiency virus envelope glycoprotein gp120. *Proc Natl Acad Sci U S A* 89, 8356-8360.

Einhorn, L., Gadler, H., and Wahren, B. (1982). Adsorption of purified human cytomegalovirus and induction of early antigens in different cells. *J Med Virol* 10, 225-234.

Geijtenbeek, T. B., Krooshoop, D. J., Bleijs, D. A., van Vliet, S. J., van Duijnhoven, G. C., Grabovsky, V., Alon, R., Figdor, C. G., and van Kooyk, Y. (2000a). DC-SIGN-ICAM-2 interaction mediates dendritic cell trafficking. *Nat Immunol* 1, 353-357.

Geijtenbeek, T. B., Kwon, D. S., Torensma, R., van Vliet, S. J., van Duijnhoven, G. C., Middel, J., Cornelissen, I. L., Nottet, H. S., KewalRamani, V. N., Littman, D. R., et al. (2000b). DC-SIGN, a dendritic cell-specific HIV-1-binding protein that enhances trans-infection of T cells. *Cell* 100, 587-597.

Geijtenbeek, T. B., Torensma, R., van Vliet, S. J., van Duijnhoven, G. C., Adema, G. J., van Kooyk, Y., and Figdor, C. G. (2000c). Identification of DC-SIGN, a novel dendritic cell-specific ICAM-3 receptor that supports primary immune responses. *Cell* 100, 575-585.

Gibson, W. (1983). Protein counterparts of human and simian cytomegaloviruses. *Virology* 128, 391-406.

Gorman et al. (1982) *P.N.A.S.* 79:6777.

Grosschedl et al. (1985) *Cell* 41:885.

Jacquet, A., Massaer, M., Haumont, M., Houard, S., Deleersnyder, V., Place, M., Bollen, A., and Jacobs, P. (1995). Purification and characterization of recombinant varicella-zoster virus glycoprotein gpII, secreted by Chinese hamster ovary cells. *Protein Expr Purif* 6, 91-98.

Jameson, B., Baribaud, F., Pohlmann, S., Ghavimi, D., Mortari, F., Doms, R. W., and Iwasaki, A. (2002). Expression of DC-SIGN by dendritic cells of intestinal and genital mucosae in humans and rhesus macaques. *J Virol* 76, 1866-1875.

Jost et al. (1994) *J.B.C.* 269:26267-73.

Kabat et al. (1991) Sequences of Proteins of Immunological Interest, N.I.H. publication no. 91-3242

Kahl, M., Siegel-Axel, D., Stenglein, S., Jahn, G., and Sinzger, C. (2000). Efficient lytic infection of human arterial endothelial cells by human cytomegalovirus strains. *J Virol* 74, 7628-7635.

Kari, B., and Gehrz, R. (1992). A human cytomegalovirus glycoprotein complex designated gC-II is a major heparin-binding component of the envelope. *J Virol* 66, 1761-1764.

Kaufmann, S. H. E. (2001). How can immunology contribute to the control of tuberculosis? *Nat. Rev. Immunol.* 1, 20-30.

Kwon, D. S., Gregorio, G., Bitton, N., Hendrickson, W. A., and Littman, D. R. (2002). DC-SIGN-Mediated Internalization of HIV Is Required for Trans-Enhancement of T Cell Infection. *Immunity* 16, 135-144.

Lashmit, P. E., Stinski, M. F., Murphy, E. A., and Bullock, G. C. (1998). A cis repression sequence adjacent to the transcription start site of the human cytomegalovirus US3 gene is required to down regulate gene expression at early and late times after infection. *J Virol* 72, 9575-9584.

Lee, B., Leslie, G., Soilleux, E., O'Doherty, U., Baik, S., Levroney, E., Flummerfelt, K., Swiggard, W., Coleman, N., Malim, M., and Doms, R. W. (2001). cis Expression of DC-SIGN allows for more efficient entry of human and simian immunodeficiency viruses via CD4 and a coreceptor. *J Virol* 75, 12028-12038.

Liu et al. (1987) *P.N.A.S.* 84:3439 and (1987) *J. Immunol.* 139:3521.

Milne, R. S., Paterson, D. A., and Booth, J. C. (1998). Human cytomegalovirus glycoprotein H/glycoprotein L complex modulates fusion-from-without. *J Gen Virol* 79 (Pt 4), 855-865.

Mitchell, D. A., Fadden, A. J., and Drickamer, K. (2001). A novel mechanism of carbohydrate recognition by the C-type lectins DC-SIGN and DC-SIGNR. Subunit organization and binding to multivalent ligands. *J Biol Chem* 276, 28939-28945.

Moody, D. B. et al. (2000). CD1c-mediated T-cell recognition of isoprenoid glycolipids in Mycobacterium tuberculosis infection. *Nature* 404, 884-8.

Navarro, D., Paz, P., Tugizov, S., Topp, K., La Vail, J., and Pereira, L. (1993). Glycoprotein B of human cytomegalovirus promotes virion penetration into cells, transmission of infection from cell to cell, and fusion of infected cells. *Virology* 197, 143-158.

Norais, N., Hall, J. A., Gross, L., Tang, D., Kaur, S., Chamberlain, S. H., Burke, R. L., and Marcus, F. (1996). Evidence for a phosphorylation site in cytomegalovirus glycoprotein gB. *J Virol* 70, 5716-5719.

Okayama et al. (1983) Mol. Cell. Bio. 3:280.

Park, C. G., Takahara, K., Umemoto, E., Yashima, Y., Matsubara, K., Matsuda, Y., Clausen, B. E., Inaba, K., and Steinman, R. M. (2001). Five mouse homologues of the human dendritic cell C-type lectin, DC-SIGN. *Int Immunol* 13, 1283-1290.

Pass, R. F., Duliege, A. M., Boppana, S., Sekulovich, R., Percell, S., Britt, W., and Burke, R. L. (1999). A subunit cytomegalovirus vaccine based on recombinant envelope glycoprotein B and a new adjuvant. *J Infect Dis* 180, 970-975.

Pietropaolo, R. L., and Compton, T. (1997). Direct interaction between human cytomegalovirus glycoprotein B and cellular annexin II. *J Virol* 71, 9803-9807.

Plachter, B., Sinzger, C., and Jahn, G. (1996). Cell types involved in replication and distribution of human cytomegalovirus. *Adv Virus Res* 46, 195-261.

Pohlmann, S., Leslie, G. J., Edwards, T. G., Macfarlan, T., Reeves, J. D., Hiebenthal-Millow, K., Kirchhoff, F., Baribaud, F., and Doms, R. W. (2001a). DC-SIGN interactions with human immunodeficiency virus: virus binding and transfer are dissociable functions. *J Virol* 75, 10523-10526.

Pohlmann, S., Soilleux, E. J., Baribaud, F., Leslie, G. J., Morris, L. S., Trowsdale, J., Lee, B., Coleman, N., and Doms, R. W. (2001b). DC-SIGNR, a DC-SIGN homologue expressed in endothelial cells, binds to human and simian immunodeficiency viruses and activates infection in trans. *Proc Natl Acad Sci USA* 98, 2670-2675.

Raftery, M. J., Schwab, M., Eibert, S. M., Samstag, Y., Walczak, H., and Schonrich, G. (2001). Targeting the function of mature dendritic cells by human cytomegalovirus: a multilayered viral defense strategy. *Immunity* 15, 997-1009.

Riegler, S., Hebart, H., Einsele, H., Brossart, P., Jahn, G., and Sinzger, C. (2000). Monocyte-derived dendritic cells are permissive to the complete replicative cycle of human cytomegalovirus. *J Gen Virol* 81 Pt 2, 393-399.

Romani, N., Gruner, S., Brang, D., Kampgen, E., Lenz, A., Trockenbacher, B., Konwalinka, G., Fritsch, P. O., Steinman, R. M., and Schuler, G. (1994). Proliferating dendritic cell progenitors in human blood. *J Exp Med* 180, 83-93.

Scheffczik, H., Kraus, I., Kiermayer, S., Bogner, E., Holzenburg, A., Garten, W., and Eickmann, M. (2001). Multimerization potential of the cytoplasmic domain of the human cytomegalovirus glycoprotein B. *FEBS Lett* 506, 113-116.

Sisk, W. P., Bradley, J. D., Leipold, R. J., Stoltzfus, A. M., Ponce de Leon, M., Hilf, M., Peng, C., Cohen, G. H., and Eisenberg, R. J. (1994). High-level expression and purification of secreted forms of herpes simplex virus type 1 glycoprotein gD synthesized by baculovirus-infected insect cells. *J Virol* 68, 766-775.

Soderberg-Naucler, C., Fish, K. N., and Nelson, J. A. (1997). Reactivation of latent human cytomegalovirus by allogeneic stimulation of blood cells from healthy donors. *Cell* 91, 119-126.

Soilleux, E. J., Morris, L. S., Lee, B., Pohlmann, S., Trowsdale, J., Doms, R. W., and Coleman, N. (2001). Placental expression of DC-SIGN may mediate intrauterine vertical transmission of HIV. *J Pathol* 195, 586-592.

Steinman, 2000.

Taupin, J. L., Acres, B., Dott, K., Schmitt, D., Kieny, M. P., Gualde, N., and Moreau, J. F. (1993). Immunogenicity of HILDA/LIF either in a soluble or in a membrane anchored form expressed in vivo by recombinant vaccinia viruses. *Scand J Immunol* 38, 293-301.

Tsutsui, Y., Sonta, S., Kashiwai, A., Nogami, T., and Furukawa, T. (1987). Viral replication in HeLa/fibroblast hybrid cells infected with human cytomegalovirus. *Arch Virol* 95, 29-40.

Weinshenker, B. G., Wilton, S., and Rice, G. P. (1988). Phorbol ester-induced differentiation permits productive human cytomegalovirus infection in a monocytic cell line. *J Immunol* 140, 1625-1631.

U.S. Pat. Nos. 5,516,637; 5,223,409; 5,658,727; 5,667,988; 5,498,538; 5,403,484; 5,571,698; and 5,625,033.

WO 90/10077.
WO 90/04036.
WO 92/02190.
WO 98/50433.
WO 98,24893.
WO 99/53049.

The entire contents of all references, patents and published patent applications cited throughout this application are herein incorporated by reference in their entirety.

What is claimed is:

1. A method of treating a cytomegalovirus (CMV) infection of a human, wherein the infection is mediated at least in part by the binding of a CMV effector molecule on the CMV virus to at least one DC-SIGN receptor selected from DC-Specific ICAM-Grabbing Nonintegrin (DC-SIGN) and DC-Specific ICAM-Grabbing Nonintegrin Related (DC-SIGNR) of the human to be treated, the method comprising:
   administering to the human a mannosylated molecule that specifically binds to the DC-SIGN receptor;
   wherein the mannosylated molecule that specifically binds to the DC-SIGN receptor is administered in an amount sufficient to inhibit binding of the CMV virus to the DC-SIGN receptor present on a cell of the human, to thereby treat the CMV virus infection.

2. A method of treating a cytomegalovirus (CMV) infection of a human, wherein the infection is mediated at least in part by the binding of a CMV effector molecule on the CMV virus to at least one DC-SIGN receptor selected from DC-Specific ICAM-Grabbing Nonintegrin (DC-SIGN) and DC-Specific ICAM-Grabbing Nonintegrin Related (DC-SIGNR) of the human to be treated, the method comprising:
   administering to the human an antibody that specifically binds to the DC-SIGN receptor;
   wherein the antibody is administered in an amount sufficient to inhibit binding of the CMV virus to the DC-SIGN receptor present on a cell of the human, to thereby treat the CMV virus infection.

3. The method of claim 2, wherein the antibody is a monoclonal antibody.

4. The method of claim 3, wherein the monoclonal antibody is humanized.

5. The method of claim 3, wherein the monoclonal antibody is Mab 1B10.2.6.

6. The method of claim 1, wherein the mannosylated molecule is mannan.

7. A method of inhibiting entry of a CMV virus into a cell of a human that expresses at least one DC-SIGN receptor selected from DC-SIGN and DC-SIGNR of the human to be treated, the method comprising administering to the human a mannosylated molecule that specifically binds to the DC-SIGN receptor;
   wherein the mannosylated molecule that specifically binds to the DC-SIGN receptor is administered in an amount sufficient to inhibit the binding of the CMV virus effector molecule to the DC-SIGN receptor, to thereby inhibit entry of the CMV virus into the cell.

8. A method of inhibiting entry of a CMV virus into a cell of a human that expresses at least one DC-SIGN receptor selected from DC-SIGN and DC-SIGNR of the human to be treated, the method comprising administering to the human an antibody that specifically binds to the DC-SIGN receptor;
   wherein the antibody is administered in an amount sufficient to inhibit the binding of the CMV virus effector molecule to the DC-SIGN receptor, to thereby inhibit entry of the CMV virus into the cell.

9. The method of claim 8, wherein the antibody is a monoclonal antibody.

10. The method of claim 9, wherein the monoclonal antibody is humanized.

11. The method of claim 9, wherein the monoclonal antibody is Mab 1B10.2.6.

12. The method of claim 7, wherein the mannosylated molecule is mannan.

* * * * *

UNITED STATES PATENT AND TRADEMARK OFFICE
CERTIFICATE OF CORRECTION

PATENT NO. : 7,427,469 B2
APPLICATION NO. : 10/700507
DATED : September 23, 2008
INVENTOR(S) : Ali Amara et al.

Page 1 of 1

It is certified that error appears in the above-identified patent and that said Letters Patent is hereby corrected as shown below:

On the title page, item (75), line 1, "Frank" should read --Franck--.

On the title page, item (75), line 5, "Nevron" should read --Bievres--.

Signed and Sealed this

Twenty-ninth Day of September, 2009

David J. Kappos
*Director of the United States Patent and Trademark Office*